(12) United States Patent
Puttlitz et al.

(10) Patent No.: US 11,717,213 B2
(45) Date of Patent: Aug. 8, 2023

(54) LOADING DEVICE FOR MEASURING STIFFNESS OF STRUCTURAL MEMBER OVER TIME, MONITORING SYSTEM, AND METHOD THEREOF

(71) Applicant: COLORADO STATE UNIVERSITY RESEARCH FOUNDATION, Fort Collins, CO (US)

(72) Inventors: Christian M. Puttlitz, Fort Collins, CO (US); Kevin M. Labus, Fort Collins, CO (US)

(73) Assignee: COLORADO STATE UNIVERSITY RESEARCH FOUNDATION, Fort Collins, CO (US)

(*) Notice: Subject to any disclaimer, the term of this patent is extended or adjusted under 35 U.S.C. 154(b) by 503 days.

(21) Appl. No.: 17/039,111

(22) Filed: Sep. 30, 2020

(65) Prior Publication Data

US 2021/0033507 A1 Feb. 4, 2021

Related U.S. Application Data

(63) Continuation-in-part of application No. PCT/US2019/025054, filed on Mar. 29, 2019.

(Continued)

(51) Int. Cl.
*A61B 5/00* (2006.01)
*G01N 3/06* (2006.01)
(Continued)

(52) U.S. Cl.
CPC .......... *A61B 5/4504* (2013.01); *A61B 5/0048* (2013.01); *A61B 5/05* (2013.01);
(Continued)

(58) Field of Classification Search
CPC ............ G01N 9/00; G01N 9/002; G01N 9/24; G01N 9/38; G01N 2009/004–008;
(Continued)

(56) References Cited

U.S. PATENT DOCUMENTS 2,356,763 A 8/1944 Keinath
3,274,527 A 9/1966 Robinson
(Continued)

FOREIGN PATENT DOCUMENTS

WO 2005104945 A2 11/2005
WO 2009146090 A1 12/2009
(Continued)

OTHER PUBLICATIONS

Extended European Search Report issued in European Appln. No. 18787095.1 dated Dec. 10, 2020.
(Continued)

*Primary Examiner* — Jonathan M Dunlap
(74) *Attorney, Agent, or Firm* — Rossi, Kimms & McDowell LLP

(57) ABSTRACT

A loading device, a monitoring system, and a method thereof can measure stiffness of a structural member (SM) and monitor progress or property thereof over time. The loading device includes two types of displacement sensors, one type being an antenna. As the SM, which is in a magnetic or electromagnetic field and electromagnetically coupled to the antenna without contact, undergoes displacement under known loads, characteristics of the electromagnetic field coupling between the antenna and the SM change over time due to the displacement of the SM. The shift in the characteristics of the electromagnetic field coupling between the antenna and the SM can be used to determine the displacement of the SM. Based on the changes in the displacement over time, diagnosis of the SM being monitored over an (Continued)

evaluation period can be made. The loading device includes at least one movable frame to apply a preload to the SM.

19 Claims, 16 Drawing Sheets

Related U.S. Application Data

(60) Provisional application No. 62/650,520, filed on Mar. 30, 2018.

(51) Int. Cl.

| | |
|---|---|
| *G01N 3/20* | (2006.01) |
| *G01D 5/20* | (2006.01) |
| *A61B 5/05* | (2021.01) |
| *G01B 7/16* | (2006.01) |
| *G01N 27/90* | (2021.01) |
| *G01N 33/483* | (2006.01) |
| *H01Q 9/16* | (2006.01) |
| *G01N 3/08* | (2006.01) |
| *G01B 7/24* | (2006.01) |

(52) U.S. Cl.
CPC ............. *G01B 7/16* (2013.01); *G01B 7/24* (2013.01); *G01D 5/202* (2013.01); *G01D 5/2013* (2013.01); *G01N 3/066* (2013.01); *G01N 3/08* (2013.01); *G01N 3/20* (2013.01); *G01N 27/9006* (2013.01); *G01N 27/9046* (2013.01); *G01N 33/4833* (2013.01); *H01Q 9/16* (2013.01); *A61B 2562/0252* (2013.01); *A61B 2562/14* (2013.01); *G01N 2203/0023* (2013.01); *G01N 2203/0032* (2013.01); *G01N 2203/0076* (2013.01)

(58) Field of Classification Search
CPC ..... G01N 2009/263; G01N 2203/0676; G01N 2203/0032; G01N 2203/005; G01N 2203/0023; G01N 2203/0076; G01N 33/4833; G01N 3/066; G01N 3/08; G01N 3/20; G01N 3/06; G01N 3/02; G01N 27/9006; G01N 27/9046; A61B 5/0048; A61B 5/0051; A61B 5/45; A61B 5/4504; A61B 5/4509; A61B 5/05; A61B 2562/0252; A61B 2562/14; G01B 7/16; G01B 7/24; G01D 5/2013; G01D 5/202; H01Q 9/16

See application file for complete search history.

(56) References Cited

U.S. PATENT DOCUMENTS

| | | |
|---|---|---|
| 3,324,714 A | 6/1967 | Simon et al. |
| 5,339,533 A | 8/1994 | Richardson |
| 5,804,738 A | 9/1998 | Bach et al. |
| 6,053,052 A | 4/2000 | Starostovic |
| 7,581,446 B2 | 9/2009 | Troxler |
| 8,278,941 B2 | 10/2012 | Kroh |
| 8,971,024 B1 | 3/2015 | Tom et al. |
| 9,326,728 B2 | 5/2016 | Demir et al. |
| 9,662,066 B2 | 5/2017 | Ledet |
| 10,641,664 B2 | 5/2020 | Puttlitz |
| 10,674,954 B2 * | 6/2020 | Puttlitz ................. G01N 3/066 |
| 10,892,558 B1 * | 1/2021 | Wolynski ............... H01Q 9/16 |
| 11,402,193 B2 | 8/2022 | Wolynski et al. |
| 2004/0139801 A1 | 7/2004 | Wilk |
| 2006/0244580 A1 | 11/2006 | Nordmeyer |
| 2007/0119266 A1 | 5/2007 | Kain |
| 2007/0186677 A1 | 8/2007 | Zunino, III et al. |
| 2010/0044574 A1 | 2/2010 | Nishino et al. |
| 2010/0201378 A1 | 8/2010 | Costanzo et al. |
| 2010/0213929 A1 | 8/2010 | Gregg |
| 2011/0152725 A1 | 6/2011 | Demir et al. |
| 2012/0126833 A1 | 5/2012 | Dooley |
| 2012/0154248 A1 | 6/2012 | Haque et al. |
| 2013/0120003 A1 | 5/2013 | Sheikman |
| 2014/0084909 A1 | 3/2014 | Pagani |
| 2014/0182388 A1 | 7/2014 | Sipila et al. |
| 2016/0282504 A1 | 9/2016 | Wilson et al. |
| 2019/0038214 A1 | 2/2019 | Mikhail |
| 2019/0320970 A1 | 10/2019 | Puttlitz |

FOREIGN PATENT DOCUMENTS

| | | |
|---|---|---|
| WO | 2013119528 A1 | 8/2013 |
| WO | 2018195437 A1 | 10/2018 |

OTHER PUBLICATIONS

Notice of Allowance issued in U.S. Appl. No. 17/146,112 dated Apr. 20, 2022.
Office Action issued in European Appln. No. 18787095.1 dated Jan. 18, 2023.
Office Action issued in U.S. Appl. No. 16/460,249 dated Aug. 30, 2019.
Keysight Technologies. "Network Analyzer Basics." Training Manual. Jul. 31, 2014: 1-94. (Year: 2014).
Megson, T.H.G. "Structural and Stress Analysis" (2nd Edition) Ch 16. 2005: 467-547. Web. Aug. 27, 2019. Elsevier. <https://app.knovel.com/hotlink/toc/id:kpSSAE0005/structural-stress-analysis/structural-stress-analysis>.
Copending U.S. Appl. No. 16/589,736, filed Oct. 1, 2019 (a copy is not included because the cited application is not yet available to the public and the Examiner has ready access to the cited application).
International Search Report issued in Intl. Appln. No. PCT/US2019/025054 dated Jun. 10, 2019.
Written Opinion issued in Intl. Appln. No. PCT/US2019/025054 dated Jun. 10, 2019.
Rho et al. "Young's Modulus of Trabecular and Cortical Bone Material: Ultrasonic and Microtensile Measurements." Journal of Biomechanics. 1993: 111-119. vol. 26, No. 2. Cited in Specification.
Stein et al. "The Human Tibia A Simplified Method of Radiographic Analysis of its Cross-Section, With Anthropometric Correlations." Annals of Biomedical Engineering. 1979: 103-116. vol. 7. Cited in Specification.
International Search Report issued in Intl. Appln. No. PCT/US2018/028590 dated Jul. 5, 2018.
Written Opinion issued in Intl. Appln. No. PCT/US2018/028590 dated Jul. 5, 2018.
Muchaidze. "Installation and performance evaluation of coaxial cable sensors for crack and corrosion detection." Masters Theses. 2011: 95 pages.
Office Action issued in U.S. Appl. No. 16/262,305 dated Jun. 28, 2019.
Notice of Allowance issued in U.S. Appl. No. 16/262,305 dated Dec. 16, 2019.
Office Action issued in U.S. Appl. No. 16/460,249 dated Dec. 23, 2019.
Notice of Allowance issued in U.S. Appl. No. 16/460,249 dated Feb. 5, 2020.
Notice of Allowance issued in U.S. Appl. No. 16/589,736 dated Sep. 4, 2020.

* cited by examiner

LOADING DEVICE FOR MEASURING STIFFNESS OF STRUCTURAL MEMBER OVER TIME, MONITORING SYSTEM, AND METHOD THEREOF

BACKGROUND

The U.S. Pat. No. 10,641,664 (hereafter Reference 1) discloses that an in-dwelling strain sensor is not needed to monitor strain applied to a structural member. Instead, it discloses using an antenna spaced from a structural member without the antenna making contact therewith.

There still remains a need for a methodology and a device/system for applying a bending load to a structural member, which can be a person's extremity for example, and measuring the deflection of the extremity due to the applied load to accurately determine the stiffness thereof over time. In normal fracture healing, stiffness of the bone-hardware construct increases over time due to calcification of the fractured callus. It would be desirable to track these changes over time to monitor the progress and predict cases of delayed unions or non-union, allowing medical professionals to take appropriate action.

The present invention addresses these needs.

SUMMARY

The present methodology and device/system can monitor a structural member (SM), for example, healing of fractured bone fixed with implanted orthopedic hardware, using two types of sensors, one of which is a non-contact type.

One aspect of the present invention is a loading device for measuring stiffness of SM. The loading device can include a frame assembly, a first driving mechanism, a first sensor, a plurality of second sensors, and a third sensor.

The frame assembly can include a distal frame, a lower or movable support, a plurality of first loading members, a plurality of SM support members, and at least one second loading member. The lower support is restable on a stable support, which can be a fixture such as a sturdy structural member or even a floor. The distal frame can be movable independently with respect to the lower support so that the first loading members can support the SM from above to apply a preload relative to the SM support members. The lower support also can be movable relative to the distal frame to apply an additional preload or a preload independently of the distal frame. The first loading members can be disposed spaced on the distal frame along a longitudinal direction of the distal frame and configured to support the SM. The SM support members can be disposed spaced on the lower support along a longitudinal direction of the lower support and configured to support the SM. Each of the at least one second loading member can be disposed between the SM support members and configured to be movable relative to the SM support members in a direction (vertically) toward and away from the distal frame, as well as longitudinally of the lower support.

The distal frame can be pivotably configured relative to the lower support (via guide rods secured to the lower support) to enable each of the first loading members to support the SM to balance the load, so that each of the first loading members support the SM evenly, while supporting the SM from one side while the SM support members support the SM from an opposite side (disposing the SM between the first loading members and the SM support members).

The loading device can further include a movable stop member adjustably mounted to the lower support and adjustable along the longitudinal direction of the lower support to allow repeat (consistently) positioning of the SM on the loading device at different testing/measurement periods.

The first loading members and the at least one second loading member are disposed facing each other, and provide a multiple-point bending configuration. The first loading members can include two first loading members and one second loading members to provide three bending points or two second loading members to provide four bending points.

The first driving mechanism can move the at least one second loading member to apply a load to the SM and create multiple bending points with respect to the first loading members and the at least one second loading member. The first driving mechanism can move the at least one second loading member toward and away from the first loading members to apply an opposing force to the SM from opposing sides.

The loading device can further include a second driving mechanism to also move the lower support relative to the distal frame. The second driving mechanism can move the lower support member, including the plurality of SM support members, to apply a preload or an additional preload to the SM.

The first sensor, which can be a load sensor, can measure a load applied by the first driving mechanism to the one second loading member. The first sensor can be disposed between the first driving mechanism and the one second loading member.

The second sensors, which can be displacement sensors, can measure a first deflection of the SM undergoing loading. Each of the second sensors can be adjustably positionable along the longitudinal direction of the distal frame. The second sensors can include three displacement sensors positioned along the length of the distal frame. Two of the three displacement sensors can be disposed adjacent to the two first loading members, and the third displacement sensors can be located at the midpoint between the two first loading members.

The third sensor can measure a second deflection of the SM without using any strain sensing device attached to the SM or contacting the SM. Specifically, the third sensor comprises an antenna disposed spaced from the SM, secured to the distal frame, and is configured to (a) induce, using a first electrical signal, a magnetic or electromagnetic field in the vicinity of the SM to create a coupling of the magnetic or electromagnetic field between the antenna and the SM, where characteristics of the magnetic or electromagnetic field coupling between the antenna and the SM are associated with a distance between the SM and the antenna, and (b) output a second electrical signal representing the magnetic or electromagnetic field coupling between the antenna and the SM, without using any strain sensing device directly attached to the SM.

The antenna can comprise a first coaxial cable including a first end and a second end. A mount can be secured to the distal frame and hold the antenna in place. Specifically, the mount is configured to maintain the first coaxial cable stationary, in relation to the distal frame, in a coil configuration between the first and second ends. The mount can include a pair of spaced plates secured to the distal frame. Each of the pair of spaced plates can include a plurality of spaced through holes, through which the first coaxial cable is kept in the coil configuration.

The antenna can be a dipole antenna that provides a S11 parameter and functions as a displacement sensor, which is of a different type from any of the second sensors. In this respect, the antenna can further include a second coaxial cable including a third end and a fourth end. The spaced through holes also keep the second coaxial cable in the coil configuration between the third and fourth ends.

The first end of the first coaxial cable can include a connector for connecting to a signal processor, such as a network analyzer, so that only the signal from the first coaxial cable is used to obtain the second deflection curve.

The first coaxial cable includes a first shield and a first center conductor, and the second coaxial cable includes a second shield and a second center conductor. The first and second shields can be electrically connected. The first center conductor at the second end and the second center conductor at the third and fourth ends can terminate without any connection. A predetermined length of the first center conductor can be exposed at the second end and the predetermined length of the second center conductor can be exposed at the fourth end. The exposed first and second conductors can be maintained substantially parallel to each other.

The stiffness of the SM can be determined from (a) a first slope of a first deflection curve obtained from the plurality of second sensors versus the applied load curve obtained from the first sensor and (b) a second slope of a second deflection curve obtained from the third sensor versus the applied load curve.

Another aspect of the present invention is a monitoring system that can measure and monitor stiffness of the SM over an evaluation period. The monitoring system can include the loading device, which uses the first sensor, the second sensors, and the antenna, a controller, and a hardware interface.

The hardware interface is configured to receive the second electrical signal from the antenna, a third electrical signal from the load sensor, and a fourth electrical signal from each of the second sensors, and convert each of the received second, third, and fourth signals that are readable by the controller.

The controller includes a memory storing instructions and a processor configured to implement instructions stored in the memory and execute a plurality of tasks, including a first determining task, a repeating task, a second determining task, and third determining task.

The first determining task receives the converted second electrical signal from the hardware interface and determines characteristics of the magnetic or electromagnetic field coupling between the antenna and the SM.

The repeating task repeats the first determining task to obtain a plurality of characteristics of the magnetic or electromagnetic field coupling between the antenna and the SM at a predetermined interval over the evaluation period.

The second determining task determines a shift in characteristics of the magnetic or electromagnetic field coupling between the antenna and the SM after each occurrence of the first determining task determining the characteristics of the magnetic or electromagnetic field coupling between the antenna and the SM at the predetermined interval, or collectively at the end of the evaluation period.

The third determining task determines a temporal change in relative displacement of the SM and determine the stiffness of the SM over the evaluation period, based on the first slope and the second slope.

The hardware interface can be a network analyzer configured to (a) output the first electrical signal to the antenna to induce the magnetic or electromagnetic field, (b) receive the second electrical signal from the antenna, and (c) also determine the characteristics of the magnetic or electromagnetic field coupling between the antenna and the SM based on the received second electrical signal.

Another aspect is a method of applying a load to measure the stiffness in the SM as the SM undergoes a displacement under a load. The method can include (a) providing the frame assembly, (b) resting the SM on the SM support members, (c) lowering the distal frame toward the SM so that the first loading members apply a preload to the SM relative to the SM support members, (d) moving the at least one second loading member to apply a load to the SM and create multiple bending points with respect to the first loading members and the at least one second loading member, (e) measuring, using the first sensor, the load applied to the SM by the at least one second loading member, (f) measuring, using the second sensors, a first deflection of the SM undergoing loading, and (g) measuring, using the third sensor, a second deflection of the SM undergoing loading without using any strain sensing device attached to the SM or contacting the SM. Again, the stiffness of the SM can be determinable from the first slope and the second slope.

The method further includes moving the lower support, which is movably disposed relative to the stable support toward the distal frame, so that the SM support members apply an additional preload to the SM.

BRIEF DESCRIPTION OF THE DRAWING

FIG. 17A illustrates the initial position/stage, FIG. 17B illustrates a preload position/stage, and FIG. 17C illustrates a loading position/stage.

DETAILED DESCRIPTION

The present loading device and monitoring system can measure the stiffness of a structural member (SM) that deflects when a force is applied.

Figure 1:
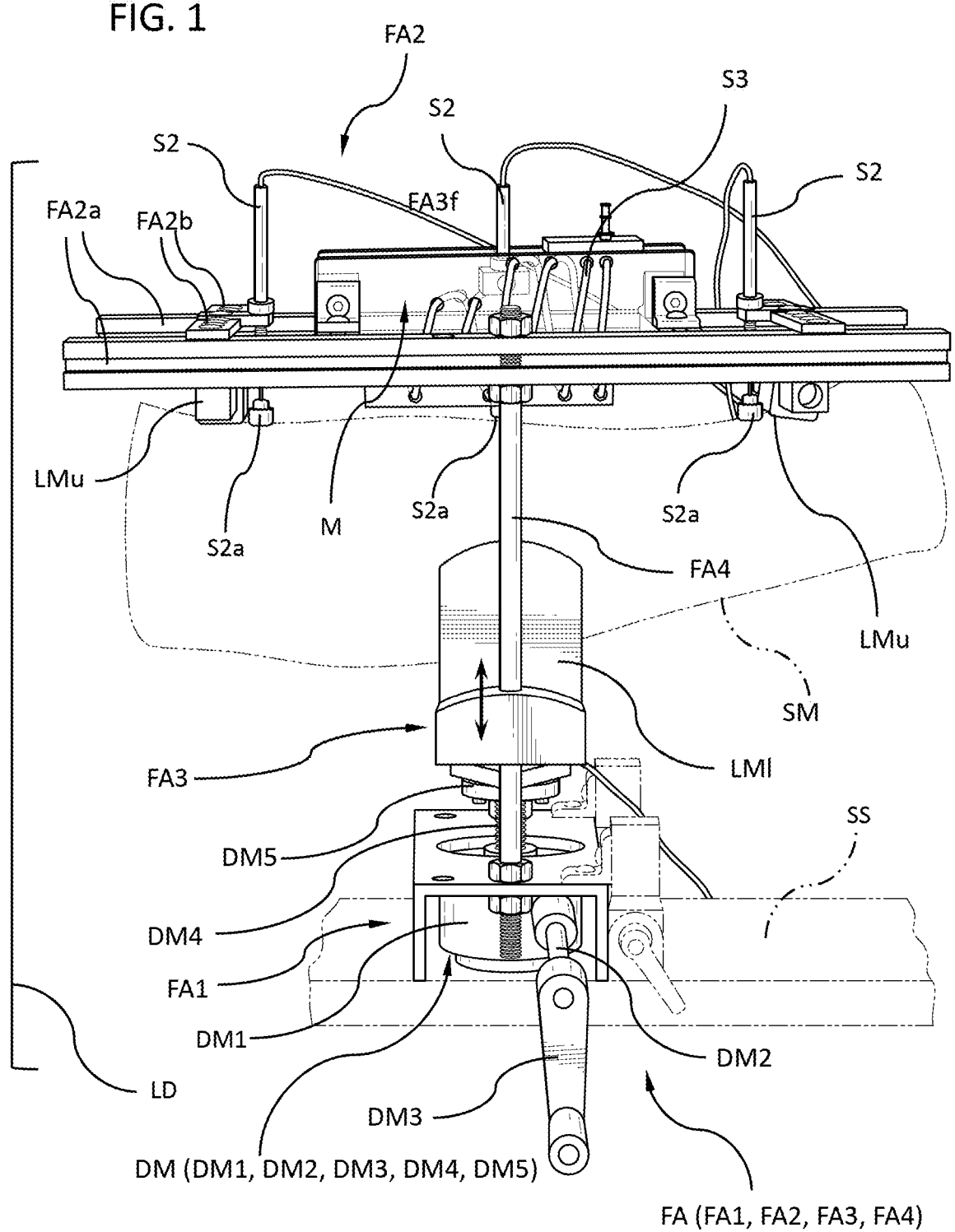
FIG. 1 illustrates an overall side perspective view of a loading device according to the present invention, with a structural member shown in phantom.

Referring to FIG. 1, the loading device LD includes a loading frame assembly FA, a driving mechanism DM, a (first) sensor S1, a plurality of (second) sensors S2, and a (third) sensor 3. The frame assembly FA can rest on a stable surface SS, such as a sturdy table or a floor, and includes upper and lower loading members LMu, LMl that act as loading points on two (opposing) sides of the SM, such as a fractured tibia fixed with an intramedullary nail or other structure support, in multiple-point bending configuration, such as a three-point bending (shown in FIGS. 1 and 16) and four point bending configuration (shown in FIG. 6). The locations of the loading points can be adjustable to accommodate various lengths of the SM. The loading members, including multiple upper (first) loading members LMu, that are positioned spaced from each other at a desired distance and rigidly mounted to the frame assembly FA, and at least one lower (second) loading member LMl, which is driven toward or away (see the double arrows in FIG. 1) from the upper loading members LMu using the driving mechanism DM secured to the frame assembly FA.

The driving mechanism DM can be a linear screw jack, which can be manually controlled by a hand crank DM3 connected to a rotating shaft DM2. The sensor S1, which can be a load sensor, such as a load cell, can be connected to a movable (lower) support or bed FA3 to measure the force applied by the driving mechanism DM.

The loading device LD in the present development uses two different types of sensors, namely a first type that makes a physical contact with the SM and/or material surrounding the SM, such as skin and tissue, and a second type that makes no physical contact with the SM or the material surrounding the SM. The stiffness of the SM can be determined from a (first) slope of a first deflection curve obtained from the plurality of sensors S2, which is one of the two sensor types, versus an applied load curve, based on the driving mechanism DM applying different loads, which is obtained from the sensor S1, and a (second) slope of a second deflection curve obtained from the sensor S3, which is the other of the two sensor types, versus the applied load curve. The second sensors S2 measure the first deflection of the SM and the third sensor S3 measures the second deflection of the SM. Combining both types of sensors allows multiple measurements of stiffness, providing for a more robust and reliable measurement system.

The frame assembly FA provides a rigid platform on which the SM can rest, and has sufficient rigidity so that any deformation it may undergo would be negligible versus the deflection that the SM undergoes when it is stressed. Specifically, the frame assembly FA includes a base FA1 that is restable on the stable support SS, a distal (upped) frame FA2 that is disposed spaced from the base FA1 at a predetermined distance, which can be adjustable, and a movable support FA3 that is configured to be movable between the base FA1 and the distal frame FA2.

Referring to FIGS. 1-6, the base FA1 and the distal frame FA2 can be made of steel, aluminum, rigid plastic, or carbon fiber material, or any combination thereof. Specifically, in the illustrated embodiments, the distal frame FA2 can be constructed from a pair of rigid main beams FA2a that are spaced apart parallel along a horizontal plane and secured in that position using a plurality of support plates FA2b and cross beams FA2c so that the main beams and the cross beams form a rigid structure that is not prone to deflection when the SM undergoes stress. The main and cross beams also can be stacked to provide an even more rigid platform. The beams can include channels/slots for anchoring bolts and nuts, such as shown in FIGS. 1-3 and 5 for attaching accessories, such as the second sensors 2 and the loading members LMu, LMl. The main and cross beams are commercially available. For example, heavy duty commercially available T-Slot aluminum extrusion rails can be used, such as available from McMaster-Carr (www.mcmaster.com/t-slotted-framing) or 80/20 Inc (8020.net/shop).

Figure 5:
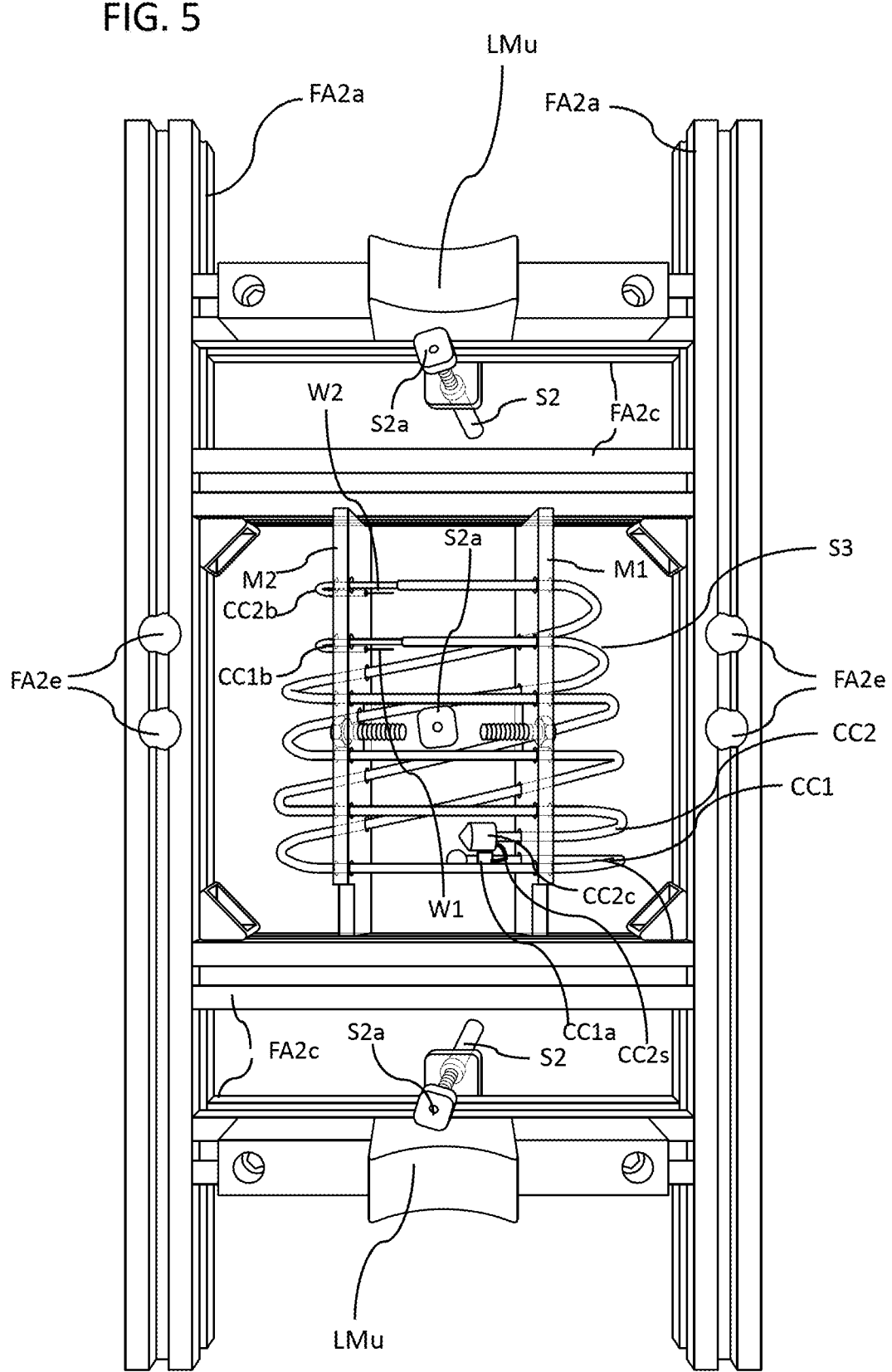
FIG. 5 illustrates a bottom view of the distal frame.

Referring to FIGS. 1 and 5, the distal frame FA2 includes the upper loading members LMu, each of which can be disposed along a length of the main beams FA2a and secured to a desired position in relation to the SM, to the cross beams FA2c using fasteners. The upper loading members LMu can be mounted to the cross beams FA2c, as illustrated in FIGS. 1 and 5. Adding more cross beams FA2c further increases the rigidity of the distal frame FA2.

Figure 2:
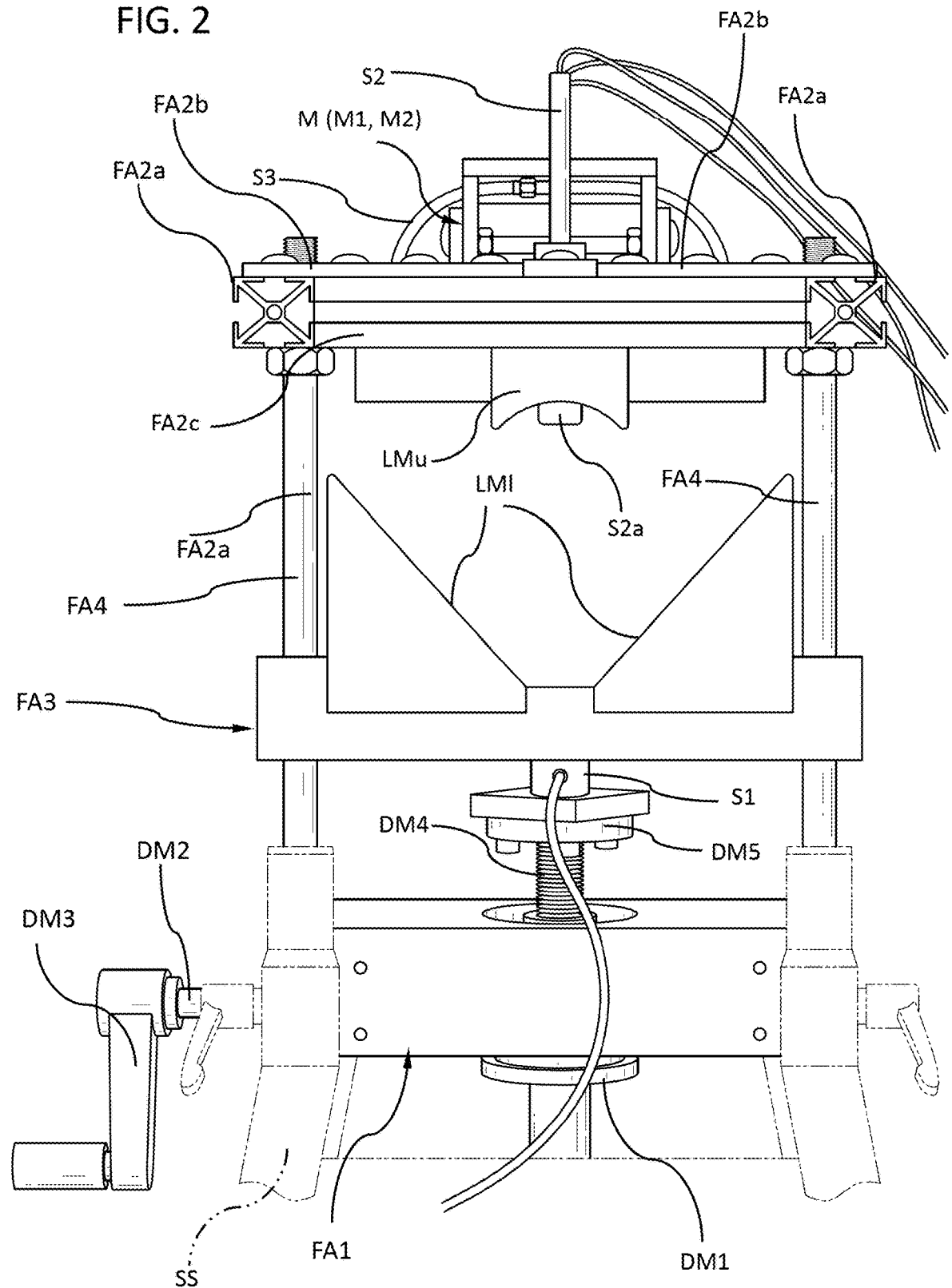
FIG. 2 illustrates a front view of the loading device.
Figure 6:
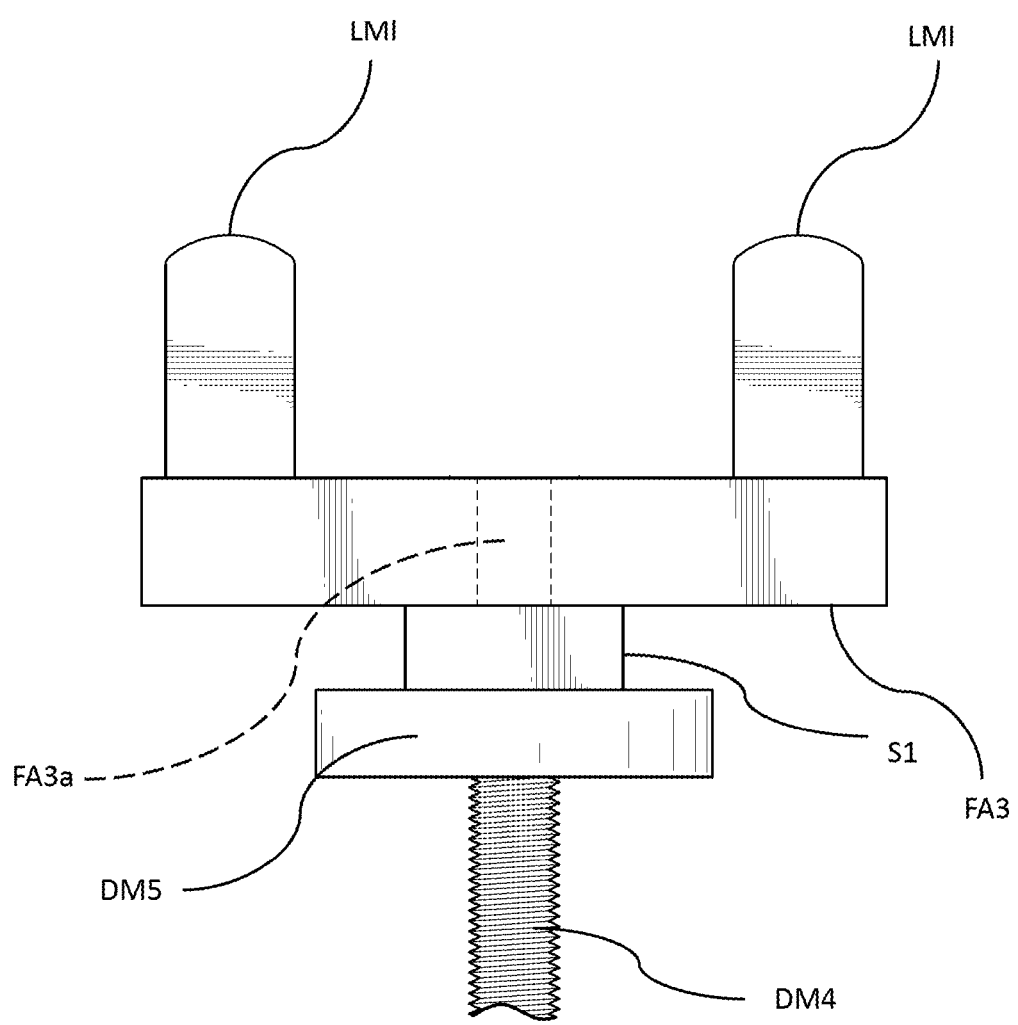
FIG. 6 illustrates an alternative embodiment of a movable support that includes multiple lower loading members to provide multiple lower loading points.

Referring to FIGS. 1-2, the base FA1 can be made from an aluminum or steel plates to rigidly mount the distal frame FA2, the movable support FA3, guide rods FA4, and the driving mechanism DM. In this respect, the base FA1 can be made from rigid material and construction that can support the movable support FA3 and the distal frame FA2, as well as the driving mechanism DM. The frame assembly FA also includes at least a pair of rigid guide rods or rails FA4 that space and maintains the distal frame FA2 spaced from the base FA1 at a desired distance, which can be adjusted, for example by replacing the guide rods having different lengths. Moreover, each guide rod FA4 can include threaded ends that can be bolted securely against the base FA1 and the distal frame FA2 and to provide a sufficient tension therebetween, as well as allowing fine height adjustments. Although the illustrated embodiment is shown with just a single pair of guide rods FA4, additional pairs of guide rods can be included, particularly when the width of the movable support FA3 becomes larger, such as when the movable support FA3 includes multiple lower bending or loading members LMl, such as schematically illustrated in FIG. 6. In this respect, each of the main beams FA2a can include at least a pair of through holes FA2e spaced along the length direction thereof each for receiving a guide rod FA4. See FIGS. 3 and 5. Similarly, the movable support FA3 also includes at least one pair of through holes FA3a each for receiving a guide rod. See FIGS. 1-3, 5, and 6. The guide rods FA4 also can be configured as described with respect to the embodiment of FIG. 16.

Moreover, the guide rods FA4 further allow the movable support FA3 to slide therealong as the movable support FA3 moves between the base FA1 and the distal frame FA2. At least one lower loading member LMl is secured to the movable support FA3. FIG. 1 shows a single lower loading member LMl and two upper loading members LMu to provide a three-point bending deflection system. FIG. 6 shows two lower loading members LMl disposed at the movable support and two upper loading members LMu to provide a four-point bending deflection system. The embodiment of FIG. 6 also can be incorporated in the embodiment of FIG. 16 to provide multiple lower loading members LMl that are movable vertically independently of the movable support FA3.

The movable support FA3, as well as each of the upper and lower loading members LMu, LMl, can be made from a block of plastic material, such as high density polyethylene, aluminum, steel, wood, or a composite material, such as carbon fiber. Each loading member LMu, LMl can be contoured to the match the shape of the SM for more stable support, and has a width that allows the SM to bend along multiple points. For example, the width of the loading members can range from 1 cm-15 cm, depending on the length of the SM.

The driving mechanism DM can be any conventional commercially available mechanical devices that can move the movable support toward or away from the distal frame FA2 (or away or toward the base FA1). For example, the driving mechanism DM can be a linear jack screw, such as a worm gear screw jack (Classic, IMA Series) available from www.seshagirigears.com or from McMASTER-CARR (www.mcmaster.com/screw-jacks). Rotating a shaft, such as using a motor or hand crank, translates a rotary motion of the crank into a linear motion, namely pushing or pulling motion.

Referring to FIGS. 1-2, a jack screw type driving mechanism can includes a main housing DM1, a driving shaft DM2, a hand crank DM3, a driven shaft DM4, a driving-worm gear (not illustrated), a driven-worm gear (not illustrated), and a support platform DM5. The driven shaft DM4 is rotatably supported and typically includes an external acme threading along the substantial length thereof. The driving-worm gear is coaxially arranged with the driving shaft DM2, which is rotatably mounted to the main housing DM1, so that it can only rotate. That is, the driving shaft is held so that it cannot move along the axial direction of the driving shaft. The driving-worm gear can have external worm gear teeth, which can be integrally formed with or mounted to the driving shaft DM2. The hand crank DM3 is mounted to the driving shaft DM2 so that rotating the hand crank rotates the driving shaft DM2, which rotates the driving-worm gear in the direction of the rotation of the hand crank.

The driven-worm gear is coaxially arranged with the driven shaft DM4 and can include external worm gear teeth that mesh with the external gear teeth of the driving-worm gear. The driven worm gear further includes an internal acme threading that meshes with the external acme threading of the driven shaft DM4. The driven-worm gear is rotatably mounted to the main housing but is prevented from moving in the axial direction of the driven shaft DM4. Thus, rotating the driven-worm gear via the driving shaft DM2 (by rotating the crank DM3) rotates the driven shaft DM4. This causes the driven shaft DM4 to move axially, either away from or toward the main housing, depending on the rotation direction of the crank. Instead of the crank, a motor can be used to drive the driven shaft using a controller or a computer.

The support platform DM5 is rotatably mounted to the distal end of the driven shaft DM4 to enable the driven shaft DM4 to rotate relative to the support platform DM5, such as using a bearing. The support platform DM5 supports the movable support FA3 so that raising the support platform DM5 raises the movable support toward the distal frame FA2.

The upper loading members LMu and the at least one lower loading member LMl, which are configured to provide multiple bending points, are disposed facing each other to apply an opposing force to the SM from the opposing sides. With the SM secured between the upper loading members LMu and the at least one lower loading member LMl, rotating the crank DM2 to rotate the driven shaft LM4 and elevate the support platform DM5 toward the distal frame FA2, moves the movable support FA3 in the same direction to apply a load to the SM.

Figure 16:
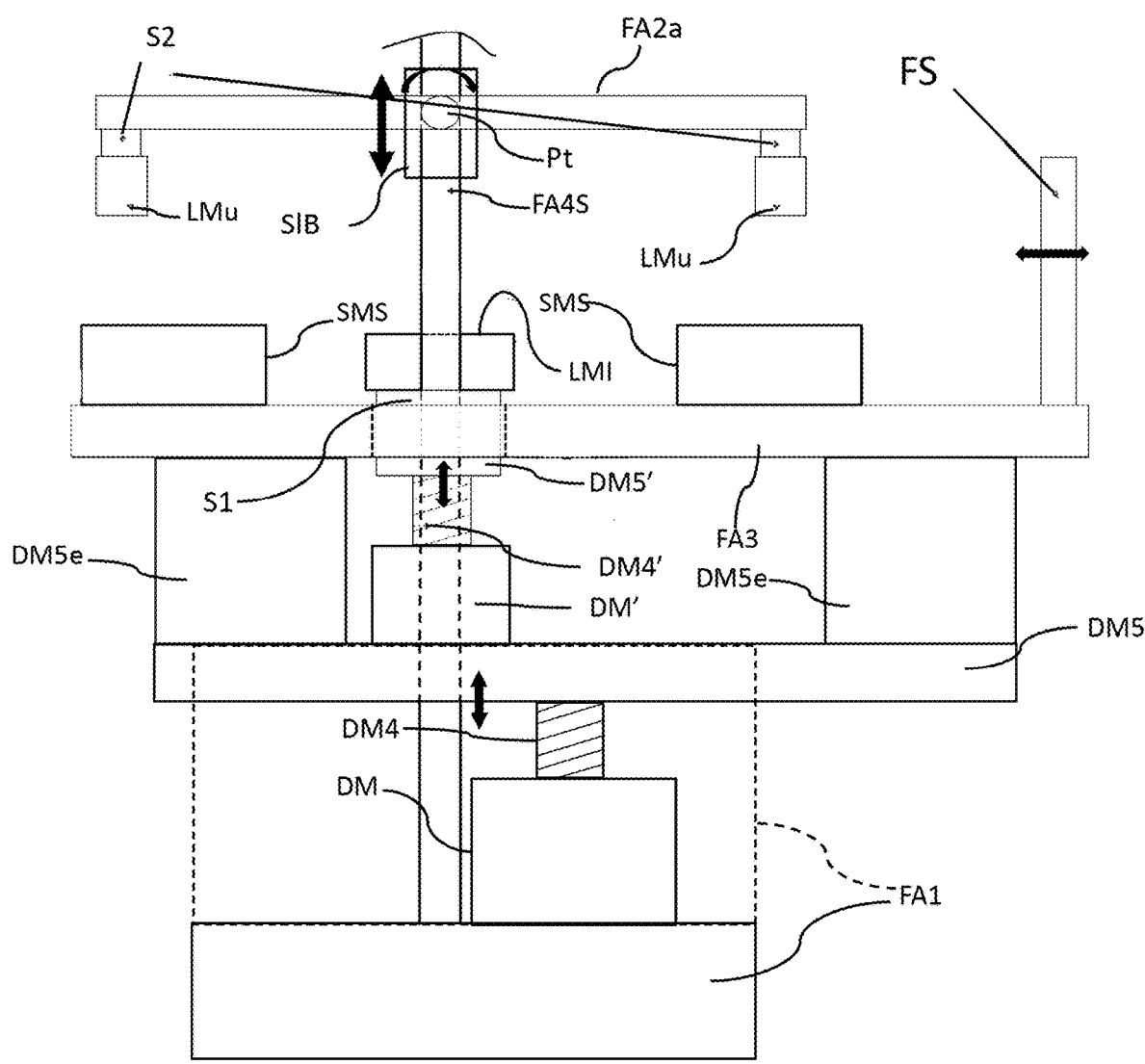
FIG. 16 illustrates another embodiment of the loading device with a lower support provided with multiple SM supporting members and at least one lower loading member to provide multiple loading points, but with a distal (upper) frame, which is provided with multiple upper loading members, that is pivotable and movable in relation to the lower support.

FIG. 16 schematically illustrates another embodiment of the loading device LD, which is based on the embodiment of FIG. 6 that uses multiple lower loading members LMl. But the embodiment of FIG. 16 includes multiple SM support members SMS and at least one loading member LMl, which is disposed between the SM support members SMS along the longitudinal direction or length thereof, that is independently movable relative to the movable support FA3 and the distal frame FA2. The base FA1, the distal frame FA2, the movable support FA3, and the driving mechanism DM previously described can be configured to be used with this embodiment. Accordingly, the details of these components have been omitted for brevity.

In the embodiment of FIG. 16, the entire distal frame FA2, including the antenna S3, sensors S2, the upper loading members LMu, itself is movable relative to the base FA1 or the movable support FA3. Specifically, the main beams FA2a are movably mounted to a pair of vertically extending opposing guide rods or beams FA4S disposed outwardly laterally thereof, so that the distal frame FA2 can be vertically moved in relation to the guide rods FA4S and locked at desired height in relation to the movable support FA3. That is, instead of each of the main beams FA2a including at least a pair of through holes FA2e spaced along the length direction thereof, each for receiving a guide rod FA4 (see FIGS. 3 and 5), a pair of vertically extending guide rods FA4S can be fixedly secured to one of the base FA1, the support platform DM5, or the movable support FA3, while being disposed laterally outside the main beams FA2a. If the guide beams FA4S are secured to the base FA1, actuating the driving mechanisms DM, DM' would not move the distal frame FA2 vertically. On the other hand, if the guide rods FA4S are secured to either the movable support FA3 or the support platform DM5, the driving mechanism DM can move the entire distal frame FA2 together with movable support FA3 as a unit. To apply an additional preload using the driving mechanism DM, the guide rods FA4S can be secured to the base FA1, as illustrated (or any fixed structure that is not movable vertically).

For example, a vertically adjustable mechanism for vertically moving the distal frame FA2 can include a pair of slider blocks SIB that each have a bore sized to slide on the respective guide rod FA4S and that are lockable thereto using, for example, one or more set screws for each slider block, to maintain the distal frame FA2 at a desired height above the movable support FA3. Each of the slider blocks SIB can be mounted to one of the main beams FA2a using the respective channel provided therein, as provided in commercial extrusions rails mentioned above, and a commercially available pivot joint that is readily mountable to extrusion rails using the slot and associated fasteners.

Moreover, the entire distal frame FA2 can be made pivotable about a pivot Pt relative to the sliding blocks SIB, using for example pivot joints or rotational bearings, such as a ball or roller bearing and shaft commercially available from McMaster-Carr or Grainger Industrial Supply, to permit the distal frame FA2 to freely pivot relative to the slider blocks SIB. The pivoting configuration allows the distal frame to rotate freely about the pivot Pt to ensure an even force distribution between the two upper loading member LMu mounted on the distal frame FA2.

Moreover, since the entire distal frame FA2 itself can move vertically, the lower support FA3 can be made stationary relative to the base FA1, namely eliminating the driving mechanism DM for the lower support FA3 and securing the lower support FA3, via the support platform DM5 and support extensions DM5e, as illustrated by phantom lines in FIG. 16. In other words, the support platform DM5 and the support extension DM5e can be part of the base when the driving mechanism DM is eliminated.

During measuring, the load is applied by raising only the lower load member LMl to apply load to the SM (e.g., leg) secured between two opposing pairs of the upper loading members LMu and the SM support member SMS. This can be achieved by disposing another driving mechanism DM', which corresponds to the driving mechanism DM in all aspects, that drives the driven shaft DM4' corresponding to the driven shaft DM4 to vertically displace the lower load member LMl and the associated sensor S1, without moving the movable support FA3.

The movable support FA3 in the embodiments of FIGS. 6 and 16 are sized larger to accommodate the SM to rest thereon, and can be moved vertically using the actuator mentioned previously, namely a manual crank driving a screw jack, an electric motor, or a pneumatic actuator. In the embodiment of FIG. 6, the movable support FA3 (while the SM is resting thereon) can apply a preload by raising it to move the SM into contact with the upper loading members LMu on the distal frame FA2. This initial pre-load sets the starting position for the bending test. In the embodiment of FIG. 16, the movable support FA3 can remain stationary while the SM is resting thereon, and the distal frame FA2 can be lowered onto the SM and locked in place to apply the initial pre-load. Although the distal frame FA2 can be actuated with a mechanical crank, electric motor, pneumatic, or other actuator, in the illustrated embodiment, gravity (weight of the distal frame FA2 itself) is used to apply the preload. When the weight of the distal frame FA2 is insufficient to reach the desired preload, the movable support FA3 can be raised upwardly with the driving mechanism DM, in a state where the guide rods FA4S are held fixed to the base FA1, while the lower loading member LMl stays below the SM (i.e., not in contact therewith) and the distal frame FA2 is locked into place. This vertically moves the support platform DMS, including all of the components secured thereto, including the support extensions DM5e, the driving mechanism DM', the movable support FA3, the lower loading member LMl, and the sensor S1 in unison.

Although FIG. 16 only illustrates a single lower loading member LMl, it should be noted that the present development is not limited thereto, as multiple lower loading members LMl can be used to provide multiple loading points similar to FIG. 6. For example, a second lower loading member LMl can be configured as two loading members LMl illustrated in FIG. 6. The two-lower loading member configuration would be positioned between the two SM supporting members SMS to provide a four-point bending setup similar to the embodiment of FIG. 6. The two lower loading members LMl can be driven by a common driving mechanism as illustrated in FIG. 6 (independently of the driving of the moving member FA3) or independently driven by furnishing a second driving mechanism DM'.

Figure 17A:
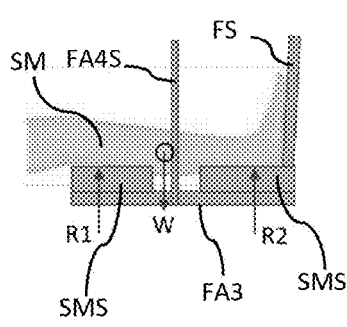
FIG. 17A-17C illustrate the loading device of FIG. 16 at three different positions/stages, where
Figure 17B:
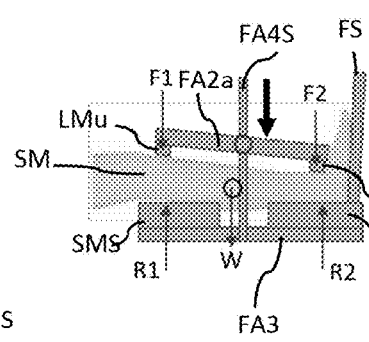
Figure 17C:
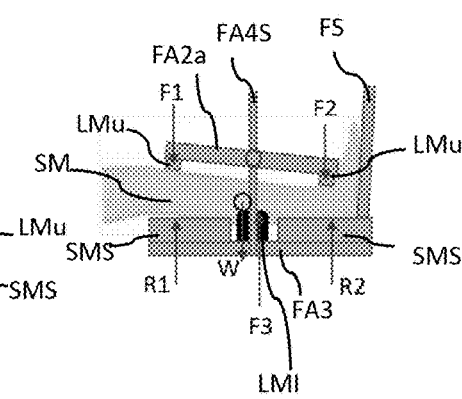

FIGS. 17A-17C show the mechanical forces W, R1, R2, F1, F2, and F3 acting on the SM, which can be a leg as an example, where W represents the weight of the SM, R1 and R2 represent the reaction forces from the SM supporting members SMS, and F1, F2, and F3 represent the measured loading forces. The maximum bending moment can be calculated at the middle of the SM (corresponding to F3) from the forces acting at the loading points.

In the embodiment of FIG. 16, the loading procedure includes the following three stages.

First, the SM is positioned to rest on the SM support members SMS with the appropriate supportable portions (e.g., calf and lower part of the leg including the foot) of the SM resting on the SM support members SMS, while the SM stop FS is adjusted to keep the part (e.g., foot) of the SM resting thereon at all times, as illustrated in FIGS. 17A-17C.

The SM stop FS is located at one end of the movable support FA3 to press the part of the SM against and set the positioning (front-to-back direction) of the SM. The SM stop FS is adjustable to account for patient-specific sizing to ensure that consistent placement is achieved for a given patient between testing sessions. That is, the positions of the upper and lower loading members LMu, LMl, the SM support member SMS, and the SM stop FS can be recorded so that the measurements can be repeated while the SM is disposed at an identical or near identical position for each measurement. The SM stop FS can be adjusted, using a similar mechanism for adjusting the position of the upper and lower loading members LMu, LMl, along the longitudinal direction of the distal frame FA2. The load sensors S1, S2 are attached to each of the loading points respectively (one lower and two upper in the embodiment of FIG. 16, similar to the embodiment of FIG. 1).

Second, the distal frame FA2 is lowered, as guided by guide rods FA4S, so that upper loading members LMu, which are positioned to oppose the SM support member SMS respectively, come to rest on the SM to apply a preload corresponding to the weight of the distal frame FA2, as illustrated in FIG. 17B. Moreover, the movable support FA3 can be elevated to raise the SM support members SMS to apply more preload in a case where the weight of the distal frame FA2 is not sufficient to apply the desired preload.

As the distal frame FA2 is freely pivotable relative to the guide rods/movable support FA3, the height of the two upper loading members can be different as illustrated in FIGS. 17B-17C, to evenly distribute the load. In this preload position, the distal frame FA2 is secured in place to the guide rods FA4S to lock the distal frame FA2 at a fixed height in relation to the movable support FA3 during testing, where the SM is disposed locked between the upper loading members LMu and the SM support members SMS.

Third, the lower loading member LMl is raised, as opposed to moving the entire movable support FA3 described with respect to the other described embodiments, using a manual crank or other mechanism described previously, to apply a load to the SM, as illustrated in FIG. 17C. That is, the driving mechanism DM' drives the lower loading member LMl independently from the driving mechanism DM for the movable support FA3. This applies a load in a three-point bending setup similarly as already described. As the SM is essentially anchored between the upper loading members LMu and the SM support members SMS, the SM is more stably supported, which can provide more accurate load measurements.

Additional force sensors can be placed in line with the contact areas of the two upper loading members LMu positioned on the distal frame to separately measure the force acting at each contact area.

After the initial positioning and the preloading are set, the bending load can be applied in cycles by raising and lowering the lower loading member LMl, while the SM is held between the upper loading members LMu and the SM support members SMS. For the entirety of the test, the resonant frequency of the antenna can be measured while the sensor displacements are being measured to calculate load cell forces for each loading contact point. The relative change in resonant frequency and/or displacement versus the measured loads are indicators of the fracture stiffness. Multiple measurements taken over time inform on the changing stiffness and the degree of fracture healing over time.

The first sensor S1 can be a conventional load cell disposed between the support platform DM5 and the movable support FA3 (in the embodiments of FIGS. 1 and 6), or between the support platform DM5' and the lower loading member LMl (in the embodiment of FIG. 16) for measuring the force applied by the driving mechanism DM or DM' to the SM. For example, the sensor S1 can be used include a load cell, such as Honeywell Model 31 (sensing.honeywell.com/test-measurement-products/miniature-stainless-steel-load-cells/model-31) and Model 41 (sensing.honeywell.com/test-measurement-products/stainless-steel-low-profile-load-cells/model-41). Specifically, the load cell can be disposed underneath the movable support FA3 or the lower loading member LMl.

The second sensors S2, on the other hand, each are mounted to the distal frame FA2 and positioned along the length thereof at desired positions, and substantially aligned centrally with the sensor S3, for measuring a deflection around the SM. Each of the sensors S2 include a contact pad S2a, which is adjustably displaceable longitudinally (e.g., perpendicular to the longitudinal direction of the distal frame FA2) to permit each pad to be in contact with the SM during measurements.

The third sensor S3, on the other hand, is a non-contact type, and uses a radio frequency antenna RFA disposed spaced from the SM and mounted to the distal frame FA2 to measure the deflection of the SM without using any strain sensing device attached to the SM and/or the material surrounding the SM. There is no contact between the SM and the antenna RFA.

As noted earlier, the present development uses two distinct types of displacement sensors S2, S3 that can be mounted to the distal frame held stationary in relation to the base FA1. In the illustrated embodiment, the first type can be three linear displacement sensors (hereafter displacement sensor), such as DVRTs (Differential Variable Reluctance Transducer) or LVDT (Linear Variable Differential Transducer), positioned along the length of the distal frame to function as linear displacement sensors to measure the displacement of the material (e.g., skin) surrounding the SM. As illustrated, two linear displacement sensors S2 are located adjacent to two upper loading members LMu while the third linear sensor S2 is located at the midpoint between the two upper loading members LMu. The two outer displacement sensors LMu can measure the baseline displacement due to compliance in the material (e.g., soft tissue) surrounding the loaded SM. The centrally located displacement sensor S2 measures the total displacement due to the material (e.g., soft tissue) compliance when loaded. Subtracting the average displacement of the two outer displacement sensors S2 from the displacement of the central displacement sensor S2 results in the deflection of the loaded SM due to bending.

The displacement sensors S2, as mentioned can be DVRTs or LVDT, which are commercially available, for example, from MicroStrain/LORD Sensing (www.microstrain.com/displacement/nodes) or Omega Engineering (www.omega.com/subsection/displacement-proximity-transducers-all.html).

Figure 7:
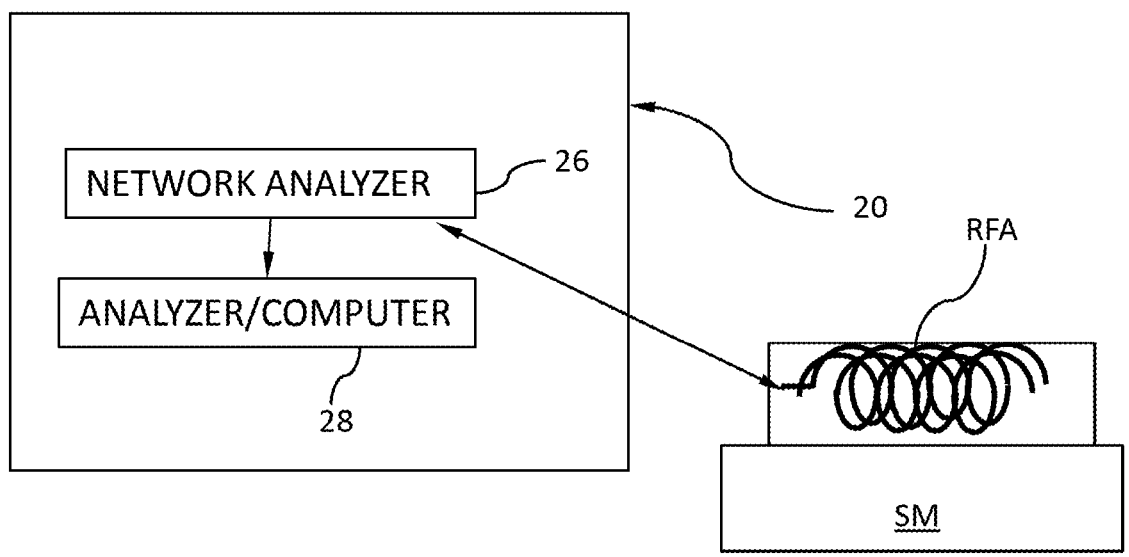
FIG. 7 schematically illustrates an embodiment of a system that can monitor changes in the structural member.

Referring to FIG. 7, the second type of deflection sensor is a radio frequency antenna RFA, which can be powered by a network analyzer 26 that includes an A/D converter. The network analyzer measures the S11 parameter (return loss) of the antenna RFA. The resonant frequency of the antenna is determined as the frequency location of the local minima of the S11 parameter dB response. That is, the antenna's resonant frequency can be determined by finding the frequency corresponding to the minimum dB of the measured S11 parameter. The antenna's resonant frequency is sensitive to the location of objects in the near field, and is especially sensitive to metallic objects. Therefore, the antenna RFA can function as a proximity sensor and can measure deflections of the SM, such as extremity together with the implanted hardware, which is typically metallic.

The deflection measured from the antenna RFA is advantageous because it does not contact the SM and measures the deflection of the construct as a whole instead of relying on skin deflection of an extremity for example. The displacement sensors S2 are advantageous because they can provide displacement measurements at multiple locations along the length of the loaded extremity, allowing for accounting displacements due to soft tissue compliance. The stiffness of the target construct can be obtained from the slope of the deflection curve versus the applied load curve.

Figure 3:
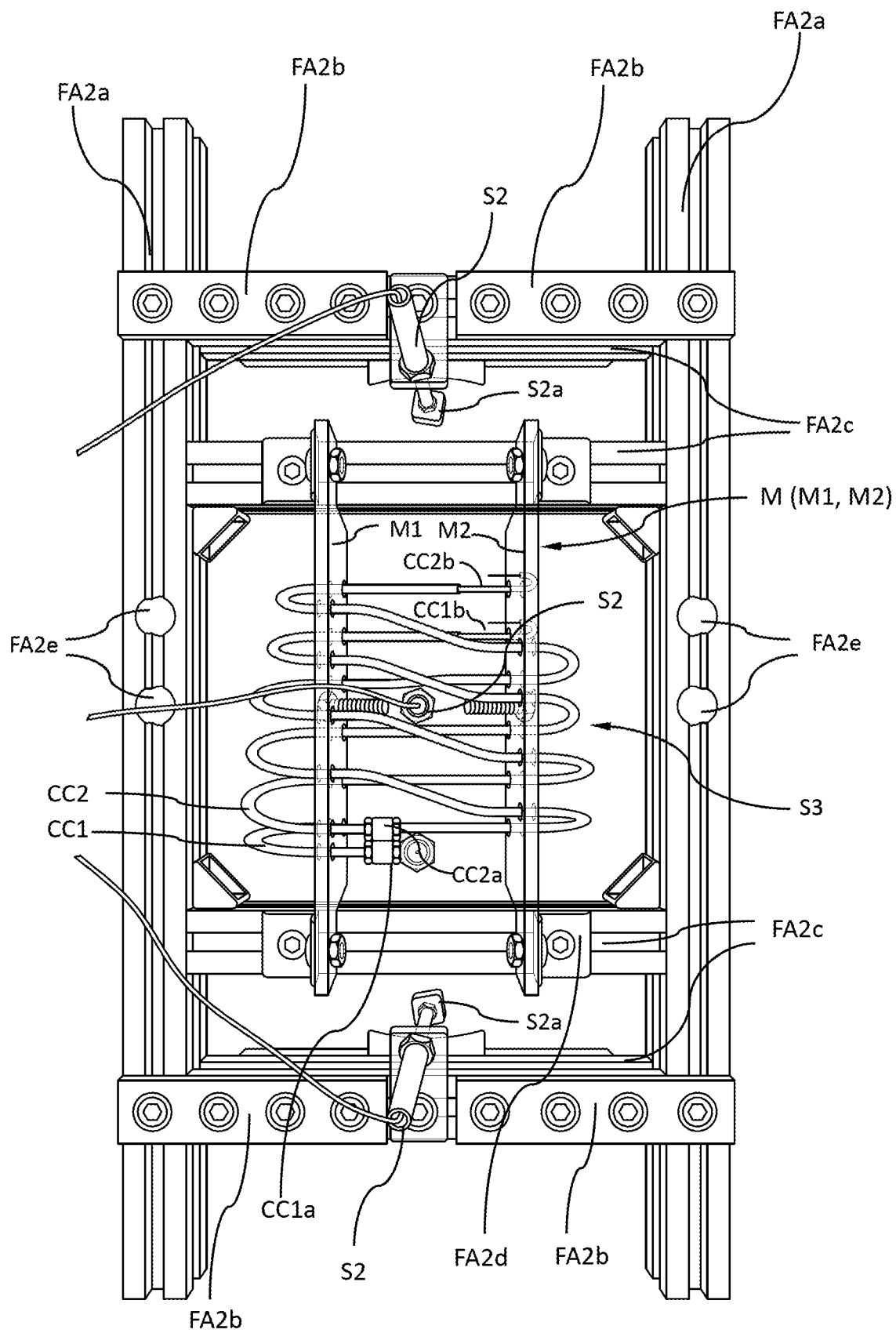
FIG. 3 illustrates a top view of a distal frame of the loading device.
Figure 4:
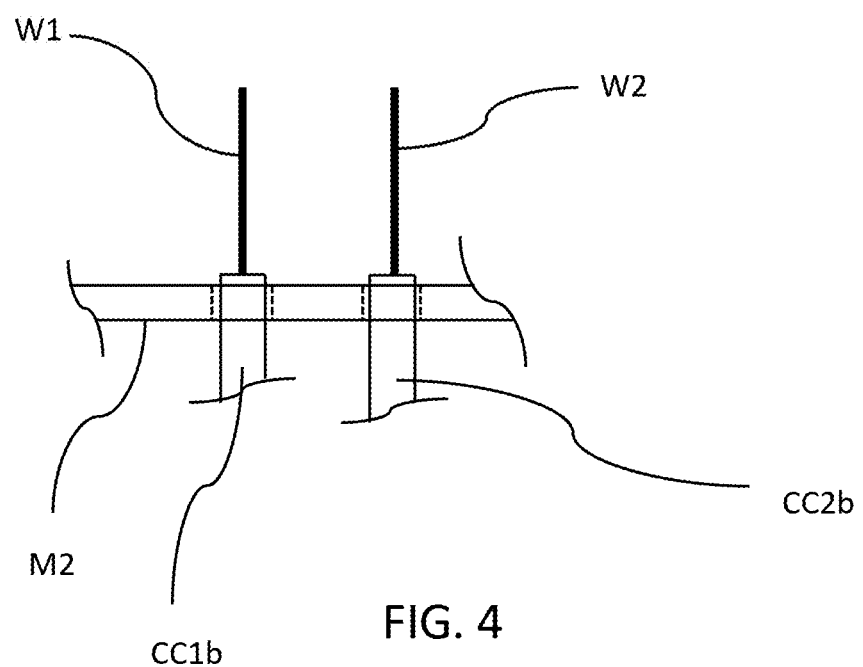
FIG. 4 illustrates an enlarged view of an antenna configuration more clearly illustrating the arrangement of the exposed center conductor of the coaxial cables.

Specifically, referring to FIGS. 3-5, the antenna RFA can have a dipole configuration, using a pair of coiled coaxial cables CC1, CC2 (although non-coiled type antennas can be used). But only one of the two cables, such as cable CC1, is connected to the network analyzer to obtain the S11 parameter. Using the center conductor W1, the S11 parameter, which can be measured with the cable CC1 connected to port 1, represents the ratio of the power sourced at port 1 that is returned back to port 1, also known as the "return loss." At the antenna's resonant frequency, the S11 parameter reaches a local minima. The outer shield of the other cable CC2 of the antenna RFA can be grounded to the outer shield of the cable CC1 that is grounded to the port 1.

For example, referring to FIG. 5, the outer shields of both coaxial cables, at one (first and third) ends thereof, can be electrically connected to each other at a coaxial connector CC1a that allows connection of an extension coaxial cable that connects to port 1 of the network analyzer. For example, this can be achieved by connecting the shield CC2s (FIG. 5) of the cable CC2 to the connector CC1a provided at the cable CC1. Alternatively, as illustrated in FIG. 3, the cable CC2 also can include another coaxial connector CC2a at the one (third) end and secure the two metal connectors so they make good contact and permit electrical connection. Alternatively, connectors CC1a can use a Y-type connector (not shown) to connect both the connectors CC1a and CC2a to ground the shields to each other. Although FIG. 5 illustrates the bottom view of FIG. 3, the embodiment of FIG. 5 includes a terminating cap CC2c instead of the connector CC2a.

It should be noted that the center conductor W2 of the cable CC2 is isolated from the coaxial connector CC1a (or the Y-type connector). At the other (second and fourth) ends of the cables CC1, CC2, the outer jackets and the shields, and any foil shields are stripped off to expose the dielectric insulators CC1b, CC2b. Moreover, referring to FIGS. 3-5, part of each exposed dielectric insulator is stripped off to expose the respective center conductors W1, W2.

Still referring to FIGS. 3-5, a mount M is installed on the distal frame FA2 using brackets FA2d and fasteners. The mount M maintains the antenna RFA in a static position in relation to the distal frame FA2. Specifically, the mount M includes a pair of spaced plates M1, M2, preferably non-metallic, that are spaced apart. The pair of plates M1, M2 include a plurality of through holes, through which the cables CC1, CC2 are inserted through to provide a coiled configuration for each of the cables CC1, CC2.

Referring to FIG. 4, which provides an enlarged schematic view of the (second and fourth) ends of the cables CC1, CC2, the exposed center conductors W1, W2 are held substantially parallel to each other. This can be achieved by securing the ends of the exposed dielectric insulators CC1b, CC2b in the pair of spaced through holes in the plate M2, such as by hot gluing them in place in the through holes, while they are aligned substantially parallel. The exposed center conductors also can be bent to position them substantially parallel to each other. This allows the center conductors W1, W2 of the two coaxial cables CC1, CC2 to interact with each other via their electric fields. These center conductors W1, W2 are spaced from each other at the second and fourth ends, but otherwise just terminate without connecting to anything. Only the center conductor W1 of the cable CC1 at the first end is used to connect to the network analyzer 26. The length of the exposed center conductors W1, W2 can be in the range 0.5 cm-20 cm. In the present embodiment, the ideal length of the exposed center conductors W1, W2 is around 4 cm.

The cable CC2 is merely a dud as, while the shields of both cables are grounded, the center conductor of the cable CC2 is not connected to the network analyzer or anything else. Although the cable CC2 is not directly used in signal analysis, it can help to eliminate noise compared to a monopole antenna. For either antenna configuration, the SM affects the frequency at which the local maxima or minima occurs when the SM is loaded.

Specifically, a metal plate or rod associated with the SM (e.g., a fractured tibia fixed with an intramedullary nail) corresponding to SM can be interrogated from the side of the coiled cables. Certain locations along the length of the coaxial cable has the greatest shift in signal. These locations depend on the resonant frequency harmonic that is measured. The coiled shape increases the signal strength by aligning the locations along the cable length where the signal is strongest. The antenna parameters can be optimized by adjusting the antenna length, spacing between coils, and resonant frequency harmonic, while interrogating a reference stainless steel bar at known distances from the antenna. Increasing the spacing between the coils increases the signal strength but also increases noise. Higher frequency harmonics also result in a stronger signal but greater noise.

Upon directing and emitting an alternating magnetic or electromagnetic field through a pre-determined frequency sweep using a source integrated in the network analyzer (or an external source if the network analyzer is not provided with the source) toward the SM, the SM interacts with the applied electromagnetic field through near field effects. The SM becomes electromagnetically coupled to the antenna RFA. The distance between the SM and the antenna can be represented by characteristics of the electromagnetic field coupling between the antenna and the SM. As the distance between the antenna and the SM changes, the characteristics of the electromagnetic field coupling between the antenna and the SM shifts because the fundamental coupling between the antenna and the SM becomes altered. For example, inducing deflection in the SM by applying a load using the driving mechanism DM changes the distance between the antenna and the SM, while the antenna RFA remains fixed in space relative to the distal frame FA2, resulting in an alteration in the resonance frequency due to changes in the electromagnetic coupling between the antenna RFA and the SM.

The S-parameters of the antenna can be obtained by the connected network analyzer 26 or the connected analyzer/computer 28. The analyzer/computer 28 can determine the resonance frequency, as well as the S-parameter magnitude of the antenna if coupled to the SM via the A/D converter, without the need for any strain sensor directly attached to the SM. If a separate source, which can be an inductor or other conventional apparatuses for applying electromagnetic fields in the radio frequency spectrum, the network analyzer can just be an A/D converter, and the analyzer/computer 28 can execute the functions of the network analyzer 26 using software.

The antenna RFA is spaced from the SM so that it does not touch any surface of the SM or the SM and/or surrounding material during the operational conditions. The electromagnetic field surrounding the antenna RFA is affected by objects in the near field range due to the conductive and/or dielectric properties of the SM. A conductive material has an eddy current induced, which in turn causes the material to act as an antenna itself, thus altering the electromagnetic field. A non-conductive dielectric material can also alter the electromagnetic field via the electromagnetic polarization of the material. Therefore, the SM can be any material that is conductive and/or has a relative permittivity (i.e., dielectric constant) that is different than the relative permittivity of the surrounding medium (e.g., air).

The components of a monitoring system 20 can include the network analyzer 26, such as a commercially-available Tektronix TTR503A Network Analyzer and Rohde & Schwarz ZVB4, which can apply electromagnetic fields in the radio frequency spectrum, the antenna interface, which includes the antenna RFA, including any wire extension extending from the antenna wires, and the analyzer 28, which can be a computer that reads and analyzes the data output from the network analyzer or stored over a period, or otherwise receives data that has been accumulated over the period. The operating frequency range of the present monitoring system can be 10 MHz to 4 GHz, with the preferred range being 40 MHz to 500 MHz for biomedical applications.

Figure 8:
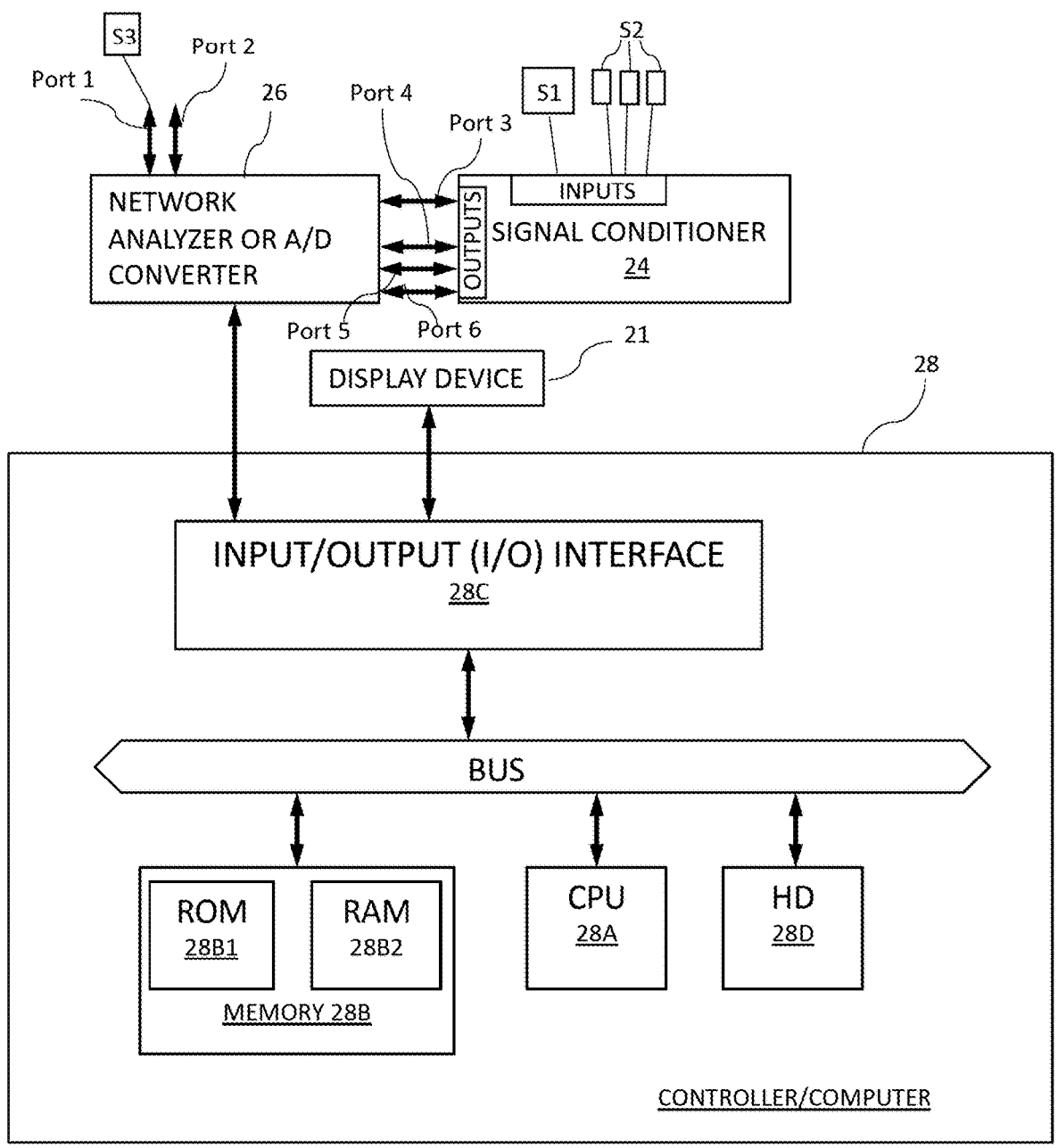
FIG. 8 illustrates a controller or computer that can determine the instantaneous or temporal change in stiffness of the structural member (over an evaluation period).

FIG. 8 schematically illustrates the analyzer 28, which comprises a controller or computer that can be programmed to analyze the shifts in the characteristics of the electromagnetic field coupling between the antenna RFA and the SM over an evaluation period or a predetermined number of measurements of the characteristics of the electromagnetic field coupling between the antenna and the SM obtained over a predetermined interval. The computer includes CPU (processor) 28A, memory 28(B), I/O (input/output) interface 28C. The I/O interface 28C can include a communication interface, such as Ethernet, for communication to a network and Internet, a display interface for connecting to a display device 21, and typical interfaces, such as USB, for connecting peripheral devices, including a keyboard and a mouse, as well as the network analyzer or any other device that can obtain the frequency sweep from the electrical signals obtained from the antenna RFA. The network analyzer 26 can be either a standalone apparatus, which can also be connected to the computer via the I/O interface 28C, or a peripheral device that converts the electrical signals from the antenna RFA into digital signals (e.g., ND converter) readable by the computer, and can be connected to the computer 28 via either the Ethernet, USB or serial port.

The computer 28 can determine the characteristics of the electromagnetic field coupling between the antenna and the SM from the electrical signal data obtained by the network analyzer 26 across a pre-determined frequency range. The functions of the network analyzer are well known and are commercially available either as a standalone unit or software operated unit using an A/D converter, such as a commercially available Tektronix TTR503A and Rohde & Schwarz ZVB4 network analyzers. Alternatively, the computer 28 can analyze the stored data of the characteristics of the electromagnetic field coupling between the antenna and the SM determined and read over an evaluation period or a predetermined number of times read over a predetermined interval by the network analyzer 26. The storage device can be a memory drive within the computer itself, flash memory, network drive, or remote database connected over the Internet.

The memory 28B communicates with the CPU 28A via a bus. The memory 28B can include a ROM 28B1 and a RAM 128B2. The memory 28B also can be configured as a non-volatile computer storage medium, such as a flash memory, instead of the RAM and the ROM. The computer 28 can also include a removable memory (e.g., flash card) connected via the I/O interface using, for example, USB or any other conventional memory card interface, and conventional hard disk 28D. The memory 28B and hard disk 28D are some embodiments of a non-transitory machine-readable medium that can store instructions, which, when executed by the processor, that perform various operations. These operations include, but are not limited to, controlling/operating the source connected to the I/O interface 28C, controlling/operating the network analyzer connected to the I/O interface 28C, determining the characteristics of the electromagnetic field coupling between the antenna RFA and the SM, determining the shift in characteristics of the electromagnetic field coupling between the antenna and the SM based on the electrical signals received from the antenna RFA in response to an electromagnetic field applied at different times over the evaluation period, and determining the temporal change in the displacement of the SM per the applied load, based on the shift in characteristics of the electromagnetic field coupling between the antenna and the SM.

Figure 9:
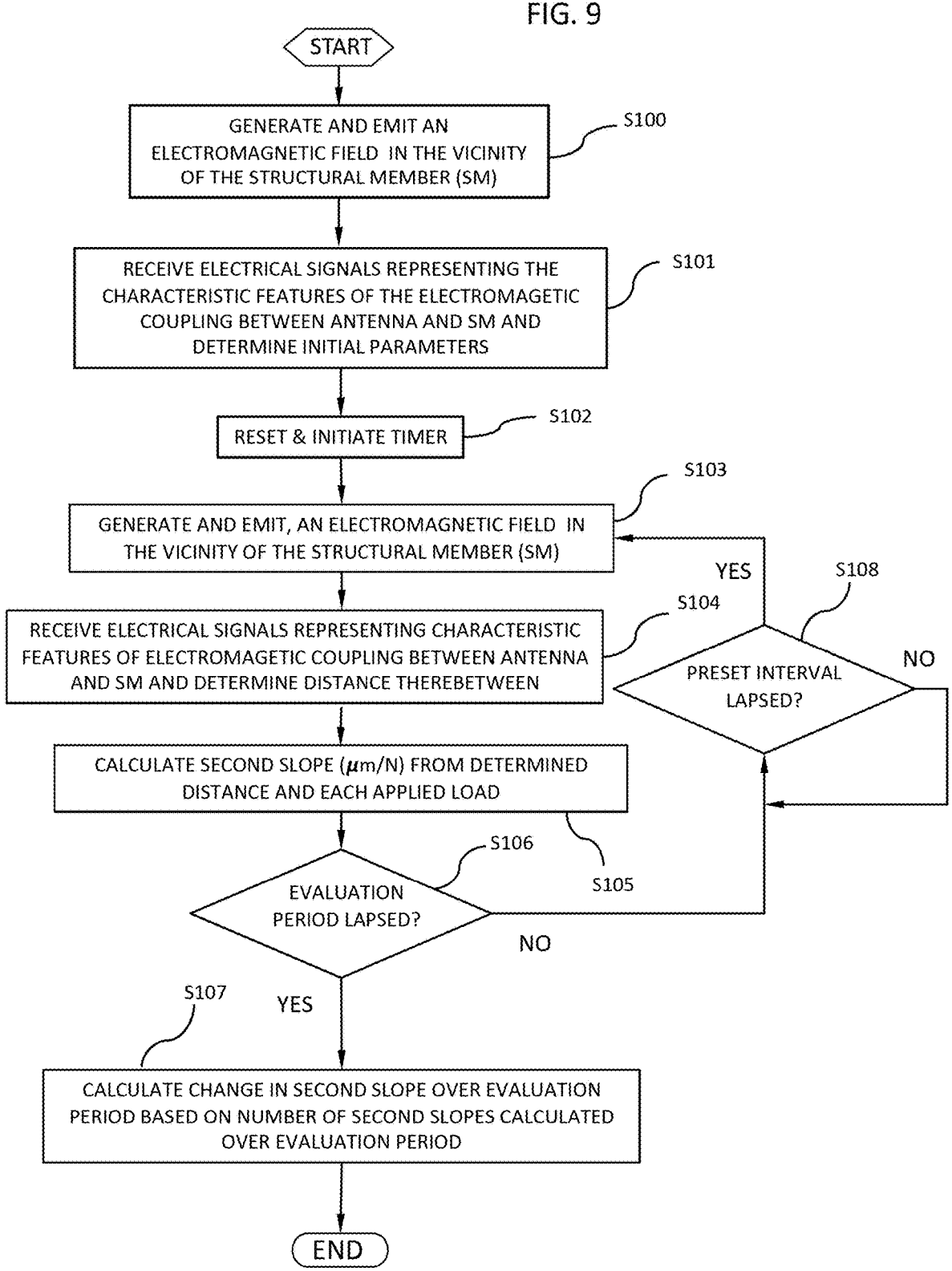
FIG. 9 illustrates an operational diagram, namely a flowchart of the present system for monitoring the stiffness in the structural member based on one sensor type (antenna).

FIG. 9 illustrates an operational flow of the monitoring system that can monitor the changes in the SM based on the antenna RFA. After the SM has been secured to the loading device, at S100, the network analyzer 26 (or the external source) is controlled to generate, emit, or direct an electromagnetic field over a pre-defined frequency bandwidth towards the SM using the antenna RFA. The SM interacts with the emitted electromagnetic field when subject to an alternating magnetic or electromagnetic field. In S101, the network analyzer 26 outputs a (first) signal to the antenna RFA, which causes the antenna RFA to output an (second) electrical signal based on the coupled electromagnetic field. The output electrical signal received from the antenna RFA is input to the network analyzer 26. After either the networks analyzer 26 or the controller determines the initial characteristics of the electromagnetic field coupling between the antenna RFA and the SM, which represents these parameters at the initial or start period, they can be stored in any of analyzer/computer 28, remote database, or local/portable storage device.

Figure 10:
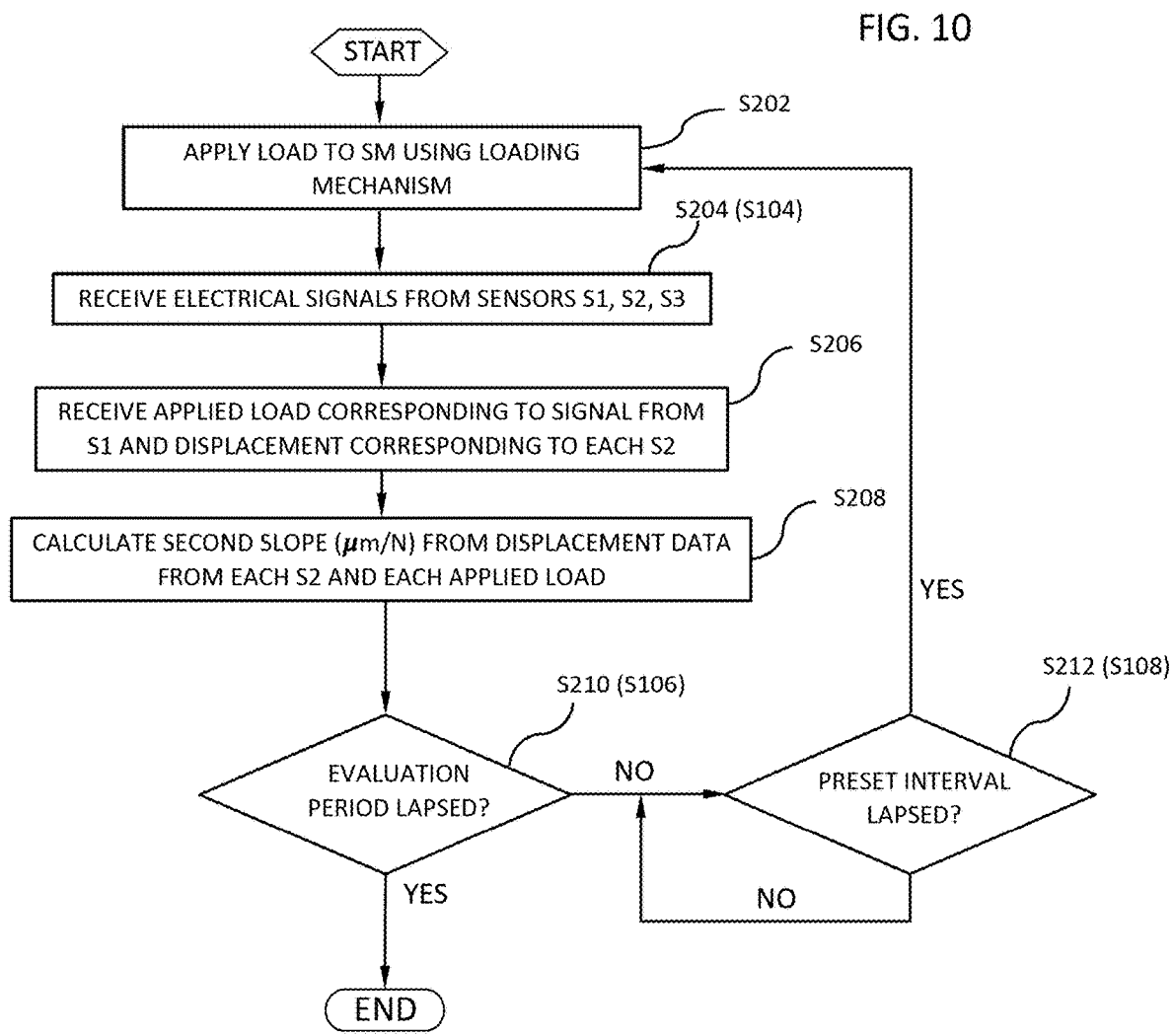
FIG. 10 illustrates another operational diagram, namely a flowchart of the present system for monitoring the stiffness in the structural member based on another sensor type (displacement sensors).

At S102, after determining the initial characteristics of the electromagnetic field coupling between the antenna RFA and the SM, a timer or a counter is reset (i.e., evaluation starting point at which the initial characteristics of the electromagnetic field coupling between the antenna RFA and the SM has been set as a reference point). For accurate positioning of the SM after setting the reference, the initially read (reference) parameters can be used as a reference to accurately position the SM for taking subsequent multiple measurements. The timer/counter can be set using the controller or a standalone timer. Alternatively, the technician monitoring the target area can keep a calendar or manually keep track of the time and date as to when the characteristics of the electromagnetic field coupling between the antenna RFA and the SM are read in relation to the applied load. At a predesigned or desired time interval after the initial characteristics of the electromagnetic field coupling between the antenna RFA and the SM have been determined, process/step S103 essentially repeats S100, and process/step S104 (corresponding to S204 in FIG. 10) repeats process/step S101 to determine the current characteristics of the electromagnetic field coupling between the antenna RFA and the SM under load applied by the driving mechanism DM.

At S105, the analyzer or computer 28 can analyze the previously determined characteristics of the electromagnetic field coupling between the antenna RFA and the SM and the currently determined characteristics of the electromagnetic field coupling between the antenna RFA and the SM and determine the shift of the characteristics of the electromagnetic field coupling between the antenna RFA and the SM by comparing the determined characteristics of the electromagnetic field coupling between the antenna RFA and the SM over different times. The shift corresponds to the change in the distance between the antenna RFA and SM during the loading. Since the data is stored, the shift in the characteristics of the electromagnetic field coupling between the antenna RFA and the SM can be determined after a predetermined number of characteristics of the electromagnetic field coupling between the antenna RFA and the SM over a desired evaluation period has been read, or after the desired evaluation period has lapsed (where a desired total number of characteristics of the electromagnetic field coupling between the antenna RFA and the SM for the desired evaluation period has been determined) (see S107). In this respect, the slope can be calculated from the change in the distance versus the applied loads (curve).

At S106 the analyzer 28 determines whether the evaluation period has lapsed or the desired total number of characteristics of the electromagnetic field coupling between the antenna RFA and the SM has been made after determining each of the characteristics of the electromagnetic field coupling between the antenna and the SM other than the determination of the initial characteristics of the electromagnetic field coupling between the antenna RFA and the SM. If the negative (NO in S106), after the preset interval, which corresponds to the duration or the interval between evaluations over the evaluation period, has lapsed (YES) at S108, processes/steps S103-S105 are repeated until affirmative in process/step S106 (YES). If affirmative (YES in S106), the analyzer 28 ends the evaluation since the evaluation period has lapsed. The temporal changes in relative displacement of the SM are determined based on the determined shift over the evaluation period. The actual temporal changes in the displacement of the SM can be determined by implementing an a priori deformation-electrical parameter or displacement-electrical parameter calibration of the hardware. Data from an electrical parameter-deformation or electrical parameter-displacement calibration, performed in advance, can be stored in memory 28B accessible by the analyzer 28.

For example, the electrical parameter signal, such as resonant frequency, can be calibrated to correspond to the distance of the antenna RFA from surface of the SM. This can be done by measuring the actual distance from the SM in relation to the resonant frequency. The resonant frequency measurement can then be used to determine the relationship between distance and resonant frequency. Because the relationship is known between the resonant frequency and the distance, the relationship can be determined between the resonant frequency and the distance. The resonant frequency measurement can therefore be calibrated to give a direct measure of the distance for that particular SM, environment, and antenna setup, namely making the antenna function as a displacement sensor.

The shift in characteristics of the electromagnetic field coupling between the antenna RFA and the SM can be used rather than the absolute values of the determined characteristics of the electromagnetic field coupling between the antenna RFA and the SM in determining the temporal relative changes in displacement of the SM. Based on the temporal changes in relative displacement of the SM, changes in the target area or biological subject can be determined. For instance, for a fracture fixation plate implanted in a person, these changes can be monitored for use in the diagnosis and the prognosis for the healing of a fractured bone for instance, or a condition of the SM.

When applying the present methodology to fracture healing, the objective is to determine the level of healing that has occurred by testing the mechanical stability of the bone-implant construct. As the healing progresses, the stiffness increases. As the stiffness increases, the deflection of the construct relative to the applied load decreases, and the signal from the antenna, such as resonant frequency shift, also decreases because it is a measure of the construct deflection. Calculating the shift in resonant frequency relative to the load applied to the bone-implant construct provides a measure of the construct stiffness and thus the shift in the mechanical stability. Therefore, the slope of the resonant frequency versus the applied load curve can be calculated. This slope is a good indicator of the stiffness. By determining this slope over time and comparing it to initial measurements, one can determine how the fracture is healing over that time frame.

This methodology is particularly useful for monitoring the relative load on the implant (due to the stiffness of the bone) at predetermined time points, such as every two weeks, throughout the healing of the fracture to monitor or predict the healing progress. As a fracture heals, the new tissue that grows progressively stabilizes the fracture, and therefore increases the relative load borne by the bone and decreases the relative load borne by the implant (orthopedic plate or intramedullary nail). As the load on the plate decreases, the deformation of the implant decreases proportionally, and the characteristics change accordingly, reflecting the stiffness of the bone. Calculating the shift in the signal, such as resonant frequency, relative to the load applied to the implant-bone construct reflects a measure of the relative load on the implant, which corresponds to the amount of deflection or change in the amount of flexing. Therefore, the signal from the antenna can be plotted against the load applied to SM and the change in the deflection amount or the amount of distance moved by the load. The slope of the resulting curve can represent the stability of the SM and the level of healing. If the fracture is not healing properly, the load on the plate changes slowly or does not change over time, which means the amount of deflection does not change. By taking temporal measurements, a physician can monitor the healing progress by determining the change in the deflection amount relative to the initial measurement. The measurement can therefore provide the physician with an early indicator whether the fracture is not healing normally and may need further treatment.

While the data from the antenna RFA is being collected, the data from the load sensor S1 and the displacement sensors S2 can be collected concurrently or serially from a signal conditioner(s) 24, which is connected to the ND converter (or network analyzer) 26 that converts the analog signals output by these sensors to digital signals via ports 3-6. Some examples of signal conditioners include, for the DVRT displacement sensors, LORD MicroStrain, model DEMOD-DC (www.microstrain.com/displacement/DEMOD-DC) or model DEMOD-DVRT (www.microstrain.com/displacement/DEMOD-DVRT-2).

The load force data output by the load sensor S1 and the deflections amount output by the displacement sensors S3 all can be tracked, while calculating the shift in signal obtained via the antenna RFA via the port 1 of the network analyzer 26. Specifically, referring to FIG. 10, at process/step S202, after the reset and the timer has been initiated in S102 in FIG. 9, the driving mechanism DM applies a desired load to start the evaluation. In process/step 204, which corresponds to S104 timewise, the network analyzer 26 receives the electrical signals from the sensors S1, S2, and S3. In process/step S206, which corresponds to S104 timewise, the network analyzer 26 receives the applied load corresponding to the signal from the load sensor S1 and the displacement corresponding to the signal from each of the displacement sensors S2. In process/step S208, the analyzer 28 calculates the slope from the displacement data (stored) from each of the displacement sensors S2 versus an applied load curve (multiple applied loads). In process/step S210, which corresponds to S106, the analyzer 28 determines whether the evaluation period or the desired total number of characteristics of the electromagnetic field coupling between the antenna RFA and the SM has lapsed. Process/step S212 corresponds to S108. If the evaluation period has not lapsed, S202-S210 are repeated until affirmative YES in S210 (i.e., the evaluation period ends). If affirmative in S210, the analyzer 28 ends the evaluation.

In the present development, testing was conducted on a bone, namely a fractured tibia fixed with an intramedullary nail or rod, which is metal. But it should be noted that the SM to be tested is not limited to bone medium, but can be applied to any structural material.

Testing I: Healthy Human Tibia

Figure 11:
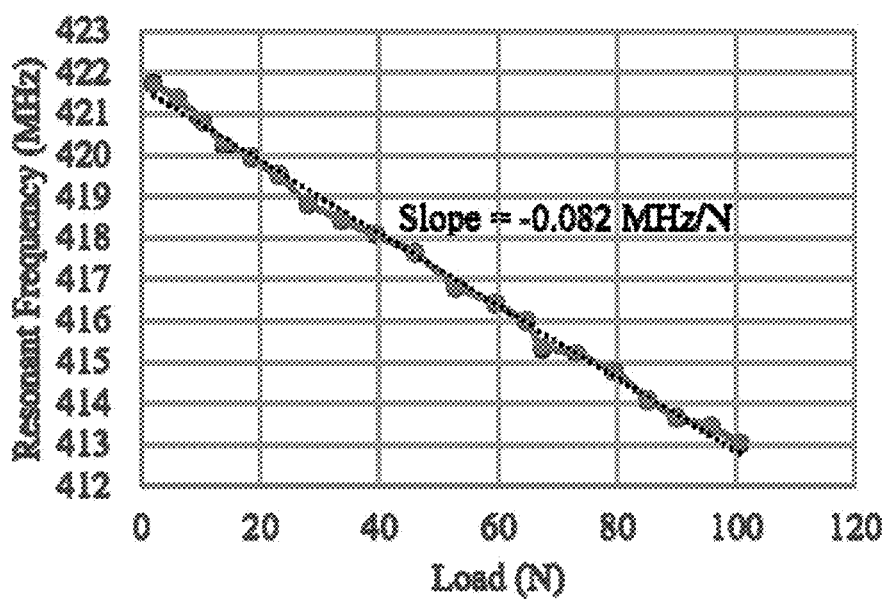
FIG. 11 illustrates an example curve showing antenna resonant frequency versus the applied load.

The loading device was tested on a healthy tibia of a volunteer. The loading frame was set in a three-point bending configuration as illustrated in FIG. 1 with the upper two loading members LMu 35 cm apart, and the lower loading member LMI at the middle thereof. The loading was applied using the driving mechanism DM for five cycles from 0 to 100 N. Separate tests were conducted using the antenna RFA and the displacement sensors S2. The antenna test showed a consistent linear response of the resonant frequency relative to the applied load, as shown in FIG. 11. The mean slope from five cycles of loading was −0.082 MHz/N, and the standard deviation was 0.0027 MHz/N, which is 3% of the mean.

The displacement sensors S2 were tested in a series of experiments to evaluate the corrected displacement measurement used to account for compliance of the soft tissue. The corrected displacement was defined as the center displacement minus the average of the two outside displacements. Experiments were conducted using three methods to achieve various degrees of compliance. First, the loading device was applied in its normal state (A). Second, the loading was applied in a padding state (B) where foam padding was added to the loading points to increase the compliance. Third, the loading device was applied in a strap state (C) where the padding was removed, and the loading points were strapped to the tested leg and tightened to decrease the compliance. The leg was loaded for five cycles, and each test was conducted for three repetitions. Slopes of the displacement/load curves were calculated for both the raw center displacement sensor's displacement and the corrected displacement.

Figure 12:
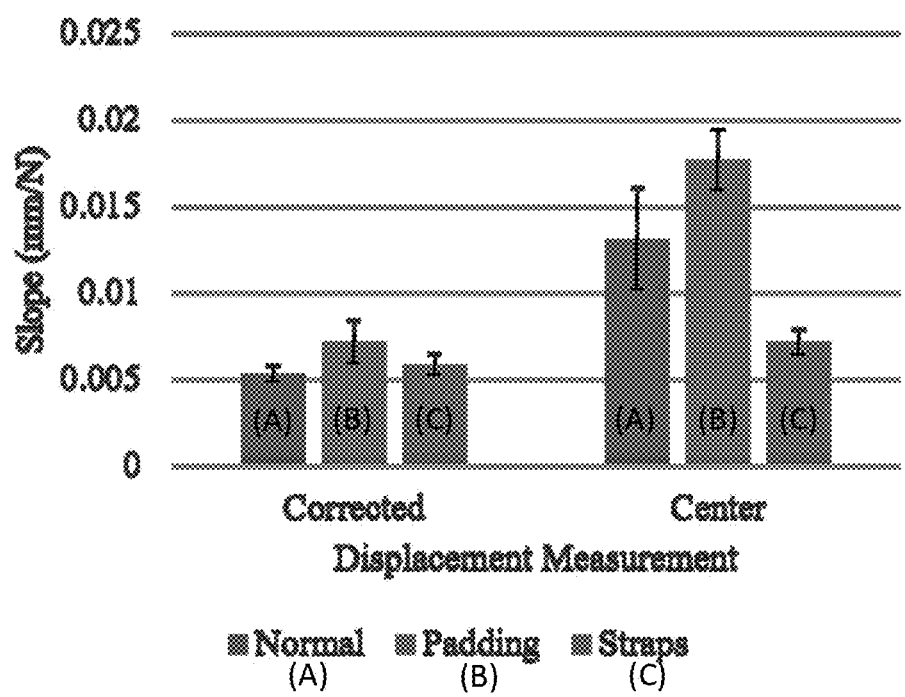
FIG. 12 illustrates slopes (mean and standard deviation) of the a linear sensor displacement versus the load curves for three compliance groups.

Referring to FIG. 12, as expected, the center displacement was highly variable between the three compliance groups (A)-(C) because the center displacement includes the displacement due to compliance and the deflection due to bending. The displacement due to compliance should be variable between the three groups, but the bending deflection was theoretically the same. Because the corrected displacement should be a measure of only the bending deflection, it should be the same between the three groups. The results showed that the corrected displacement was less than the center displacement and had lower standard deviations than the center displacement. There were also smaller differences between the three groups for the corrected displacement, compared to the center displacement. The range of the three groups was 30% of the mean, and 83% of the mean for the corrected and center displacements, respectively. The corrected displacement therefore is an improvement over the raw center displacement for lowering the variability and accounting for changes in compliance.

Additional experiments used the corrected displacement sensors displacement method to test three loading configurations, where the two upper loading members were spaced 35 cm, 23 cm, and 18 cm apart, while using a single lower loading member located centrally of the two upper loading members. Changing the spacing changes the applied bending moment relative to the applied load, while changing the deflection due to bending. Experimental results were compared to analytical solutions of beam defection (δ) due to three-point bending, which were calculated using the equation:

$$\delta = \frac{Pl^3}{48EI},$$

where P is the applied load, l is the length between the upper loading points, E=20 GPa is the elastic modulus of cortical bone according to *Young's Modulus of Trabecular and Cortical Bone Material: Ultrasonic and Microtensile Measurements*, Jae Young Rho, Richard B. Ashman, and Charles H. Turner, 1993 Journal of Biomechanics, Volume 26, Issue 2: pp. 111-119, and I=1.5 $E^{-8}$ $m^4$ is the area moment of inertia of a human tibia according to *The Human Tibia A Simplified Method of Radiographic Analysis of its Cross-Section, with Anthropometric Correlations*, Ira D. Stein and Gerald Granik, 1979 Annals of Biomedical Engineering, Volume 7, pp. 103-116.

Figure 13:
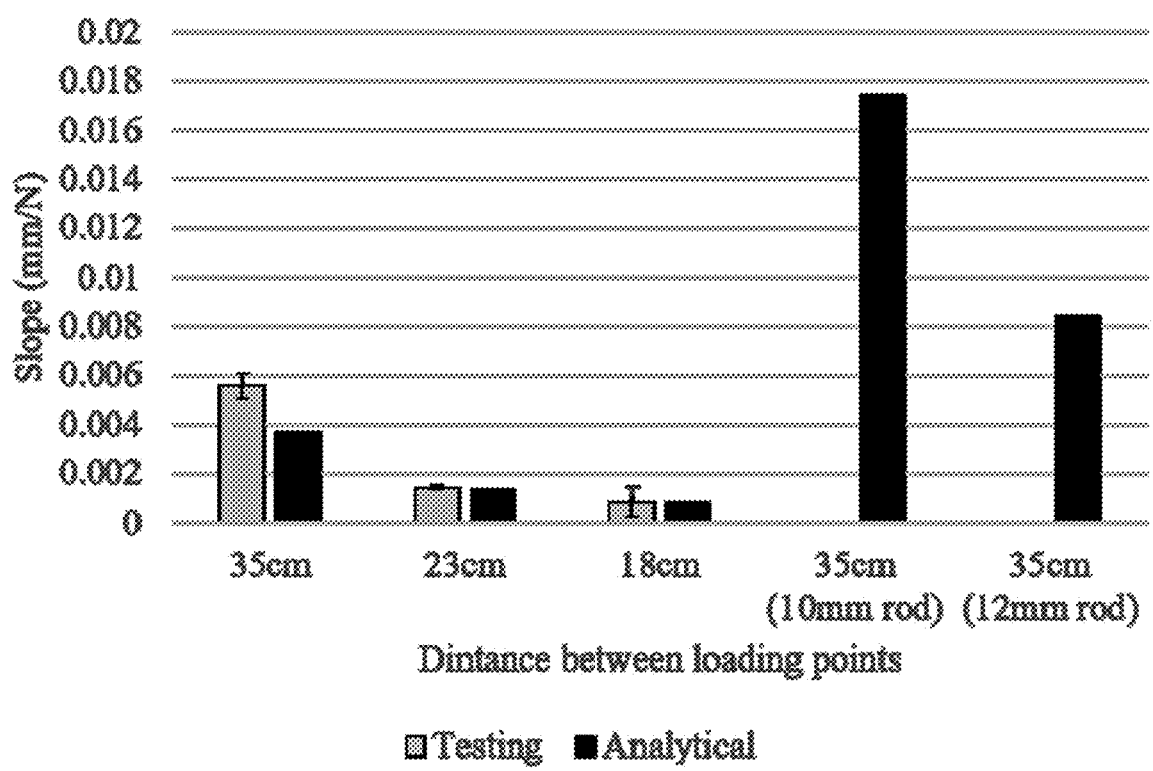
FIG. 13 illustrates sloped (mean and standard deviation) of the corrected displacement versus the load curves for the different loading point distances and for intramedullary rods representing an unhealed fracture.

Analytical solutions were also calculated for titanium rod of 10 mm and 12 mm diameters representing an unhealed (post-operational) fracture fixed with an intramedullary rod to compare the testing results on an intact tibia to the expected results for a fractured tibia. The experimental results showed relatively good agreement with the analytical solutions in FIG. 13. Discrepancies were likely due to the moment of inertia and elastic modulus properties assumed in the analytical solution, which can be highly variable. Large differences were seen between the analytical solutions for the intact tibia and the fractured tibia (intramedullary rod), indicating that differences in the bone deflection can be tracked over time as a fracture heals.

Further, the LVDTs measured displacement of the surface of the leg at the middle of the leg and adjacent to the upper loading points near the knee and ankle were determined using the embodiment of FIG. 16. The relative displacement can be calculated as the middle displacement subtracted by the average of the knee and ankle displacements. During testing, the middle lower loading point (F3) was loaded in five cycles between 30 N and 80 N force. The leg (SM) was removed from the loading device, and the measurement process was repeated eight times to test the repeatability. The measured preload from the upper loading points (F1 and F2) was about 11 N at either point. That is, the F1 and F2 forces were nearly identical, which was the intention of allowing the distal frame FA2 to freely pivot. The relationship between the upper loading forces (F1 and F2) and the lower loading point force (F3) was nonlinear at low loads due to the changing magnitude of the reaction forces at the leg (R1 and R2) as the load increased. At F3, forces greater than 30 N, the relationship between the forces was relatively linear.

The testing showed a consistent and linear relationship between antenna resonant frequency and load/bending moment and between LVDT displacement and load/bending moment. The resonant frequency-moment curves had a mean slope from the eight repetitions of 0.21 MHz/Nm, and a standard deviation of 0.022 MHz/Nm. These repetitions had a coefficient of variance of 10%. On the other hand, the same repetition experiment performed with the embodiment of FIG. 1, which did not include the leg support platform, foot-stop, pre-loading, or rotating distal frame features, on the same volunteer user had a coefficient of variance of 25%. The embodiment of FIG. 16 thus provided a substantial improvement in measurement repeatability. The relative LVDT displacement versus moment curves had a mean slope of 0.068 mm/Nm, a standard deviation of 0.0057 mm/Nm, and a coefficient of variance of 8%.

Testing II: Fracture Model of Sheep Tibia

Figure 14:
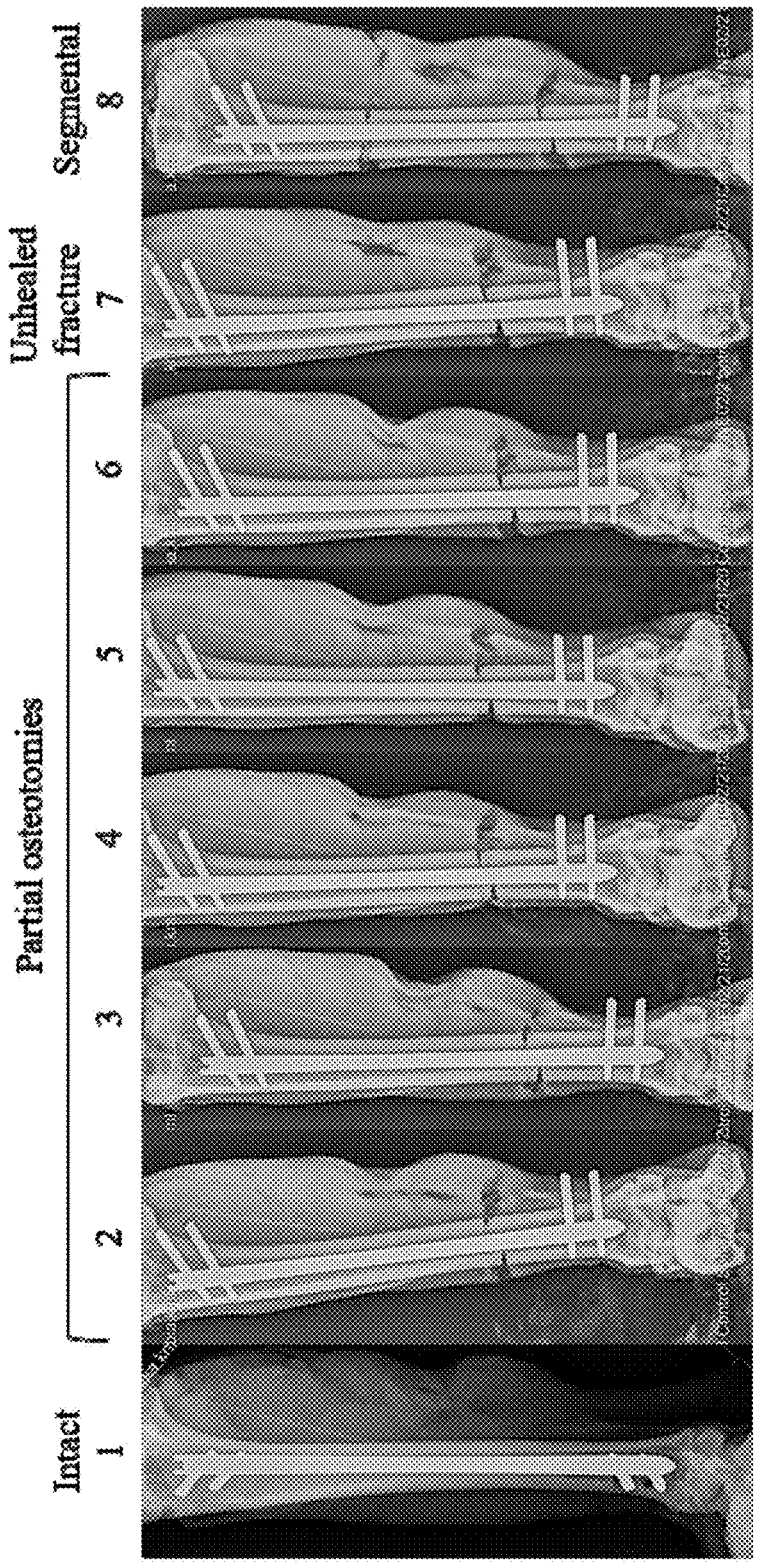
FIG. 14 illustrates radiographs of the eight testing conditions of a sheep tibia showing progressively destabilizing osteotomies.

The loading device was also tested on a cadaveric sheep tibia with an implanted intramedullary rod. The tibia was tested in eight conditions to simulate various stages of fracture healing. The first test was conducted with rod implanted in an intact bone. For tests two through six, progressively larger osteotomies were made to simulate a partially healed transverse diaphyseal fracture. For test seven, the osteotomy was extended entirely through the cross section of the bone to simulate an unhealed (post-operational) fracture. For test eight, a second complete osteotomy was made to simulate an unhealed segmental fracture. Radiographs were used to guide and confirm the osteotomies. See FIG. 14.

The loading device was configured in three-point bending deflection with the two upper loading members spaced 18 cm apart and a single lower loading member located centrally of the two upper loading members. Deflection data were collected from the antenna RFA and the displacement sensors S2 simultaneously. In each test, the bone was loaded from 30 N to 130 N for five cycles, and slopes were calculated from the corrected displacement sensor displacement versus load curves and the antenna resonant frequency versus the same load curves.

Figures 15A, 15B:
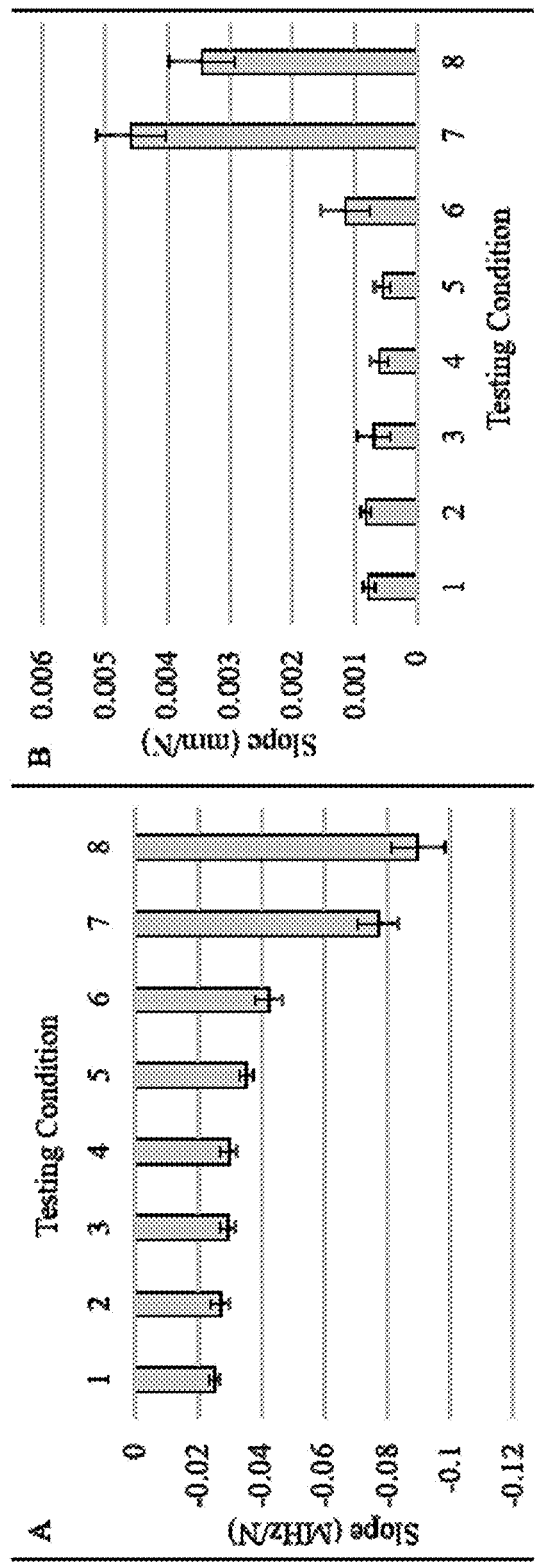
FIGS. 15A-15B illustrate slopes (mean and standard deviation) of the (A) antenna resonant frequency versus load curves, and (B) corrected linear sensor displacement versus the load curves.

Referring to FIGS. 15A-15B, results using the antenna data showed that the resonant frequency shift increased relative to the applied load with each progressive osteotomy condition, indicating that the slope of the resonant frequency versus the load curve was able to track the decreased stiffness of the bone-rod construct as it was progressively destabilized. The displacement sensor data showed a similar trend to the antenna data, where the slope of the displacement versus the same load curve was higher in tests six through eight than tests one through five. But the slopes did not increase in each of the first five tests test like they did for the antenna data. Also, tests eight (segmental fracture) had a lower displacement/load slope than test seven (single fracture).

The greater variability in the displacement sensor data than the antenna data can be attributed to the displacement sensor measuring skin displacement, whereas the antenna RFA measures the combined deflection of the bone, soft tissue, and implanted metal rod, and is especially sensitive to metal materials. The large amount of soft tissue around the sheep tibia relative to typical human tibias may have contributed to the variability in the displacement sensor data. Also, the displacement/load slope was likely lower for test eight than test seven because the center displacement sensor S2 was located over the loose segment of the segmental fracture and did not displace as much, despite the more destabilized structure. But the antenna data did track the increased destabilization of test eight as an increased slope in the resonant frequency versus the load curve. Overall, these results indicate that the present device is capable of tracking changes in construct stiffness for a fractured bone fixed with orthopedic hardware, especially using the antenna deflection measurement method.

In short, the above tests showed that the using both sensor types can monitor fracture healing progress over time. The present development can be effectually used to monitor the healing of, in particular, a fractured bone that has been fixed with implanted orthopaedic hardware. In normal fracture healing, stiffness of the bone-hardware construct increases over time due to calcification of the fractured callus. In particular, the present development can track these changes over time to monitor the healing process and predict cases of delayed unions or non-union, to allow medical professionals to take appropriate action.

Given the present disclosure, one versed in the art would appreciate that there may be other embodiments and modifications within the scope and spirit of the present invention. Accordingly, all modifications attainable by one versed in the art from the present disclosure within the scope and spirit of the present invention are to be included as further embodiments of the present invention. The scope of the present invention accordingly is to be defined as set forth in the appended claims.

What is claimed is:

1. A loading device for measuring stiffness of a structural member (SM), the loading device comprising:
a frame assembly including:
a lower support restable on a stable support;
a distal frame movable with respect to the lower support;
a plurality of first loading members disposed spaced on the distal frame along a longitudinal direction of the distal frame and configured to support the SM;
a plurality of SM support members disposed spaced on the lower support along a longitudinal direction of the lower support and configured to support the SM; and
at least one second loading member disposed between the plurality of SM support members and configured to be movable relative to the plurality of SM support members in a direction toward and away from the distal frame;
a first driving mechanism that moves the at least one second loading member to apply a load to the SM and create multiple bending points with respect to the plurality of first loading members and the at least one second loading member;
a first sensor that measures a load applied by the first driving mechanism to the at least one second loading member;
a plurality of second sensors that measure a first deflection of the SM undergoing loading;
a third sensor that measures a second deflection of the SM undergoing loading without using any strain sensing device attached to the SM or contacting the SM,
wherein the stiffness of the SM is determinable from:
a first slope of a first deflection curve obtained from the plurality of second sensors versus an applied load curve obtained from the first sensor; and
a second slope of a second deflection curve obtained from the third sensor versus the applied load curve.

2. The loading device according to claim 1, wherein the distal frame is configured to be movable toward the lower support so that the plurality of first loading members apply a preload to the SM relative to the plurality of SM support members.

3. The loading device according to claim 2, wherein the distal frame is pivotable relative to the lower support to enable each of the plurality of first loading members to support the SM from one side while the plurality of SM support members support the SM from an opposite side to secure the SM between the plurality of first loading members and the plurality of SM support members.

4. The loading device according to claim 3, further comprising a movable stop member mounted to the lower support and configured to be adjustable along the longitudinal direction of the lower support to consistently position the SM on the loading device at different times.

5. The loading device according to claim 2, further comprising:
a second driving mechanism,
wherein the lower support is movably disposed relative to the stable support and the distal frame, and
wherein the second driving mechanism is configured to move the lower support member, including the plurality of SM support members, to apply an additional preload to the SM.

6. The loading device according to claim 5, wherein the distal frame is pivotable relative to the lower support to enable each of the plurality of first loading members to support the SM from one side while the plurality of SM support members support the SM from an opposite side to secure the SM between the plurality of first loading members and the plurality of SM support members.

7. The loading device according to claim 6, further comprising a movable stop member mounted to the lower support and configured to be adjustable along the longitudinal direction of the lower support to consistently position the SM on the loading device at different times.

8. The loading device according to claim 1, further comprising:
a second driving mechanism,
wherein the lower support is movably disposed relative to the stable support and the distal frame, and
wherein the second driving mechanism is configured to move the lower support member, including the plurality of SM support members, to apply a preload to the SM.

9. The loading device according to claim 8, wherein the second driving mechanism moves the plurality of SM support members toward the plurality of first loading members to apply an opposing force to the SM from opposite sides.

10. The loading device according to claim 1, wherein the third sensor comprises an antenna disposed spaced from the SM, secured to the distal frame, and configured to:
induce, using a first electrical signal, a magnetic or electromagnetic field in the vicinity of the SM to create a coupling of the magnetic or electromagnetic field between the antenna and the SM, where characteristics of the magnetic or electromagnetic field coupling between the antenna and the SM are associated with a distance between the SM and the antenna; and
output a second electrical signal representing the magnetic or electromagnetic field coupling between the antenna and the SM, without using any strain sensing device directly attached to the SM.

11. The loading device according to claim 10, wherein the antenna is a dipole antenna that provides a S11 parameter, and functions as a displacement sensor.

12. The loading device according to claim 10, further comprising:
a mount secured to the distal frame and holding the antenna,
wherein the antenna comprises a first coaxial cable including a first end and a second end,
wherein the mount is configured to maintain the first coaxial cable stationary, in relation to the distal frame, in a coil configuration between the first and second ends.

13. A monitoring system for monitoring measuring stiffness of a structural member (SM) over an evaluation period, the system comprising:
a loading device comprising:
a frame assembly including:
a lower support restable on a stable support;
a distal frame movable with respect to the lower support;
a plurality of first loading members disposed spaced on the distal frame along a longitudinal direction of the distal frame and configured to support the SM;
a plurality of SM support members disposed spaced on the lower support along a longitudinal direction of the lower support and configured to support the SM; and
at least one second loading member disposed between the plurality of SM support members and configured to be movable relative to the plurality of SM support members in a direction toward and away from the distal frame;
a first driving mechanism that moves the at least one second loading member to apply a load to the SM and create multiple bending points with respect to the plurality of first loading members and the at least one second loading member;
a first sensor that measures a load applied by the driving mechanism to the at least one second loading member;
a plurality of second sensors that measure a first deflection of the SM undergoing loading;
an antenna that measures a second deflection of the SM undergoing loading without using any strain sensing device attached to the SM or contacting the SM,
wherein the antenna is configured to:
induce, using a first electrical signal, a magnetic or electromagnetic field in the vicinity of the SM to create a coupling of the magnetic or electromagnetic field between the antenna and the SM, where characteristics of the magnetic or electromagnetic field coupling between the antenna and the SM are associated with a distance between the SM and the antenna; and
output a second electrical signal representing the magnetic or electromagnetic field coupling between the antenna and the SM, without using any strain sensing device directly attached to the SM;
a controller including a memory storing instructions and a processor configured to implement instructions stored in the memory and execute a plurality of tasks;
a hardware interface configured to receive the second electrical signal from the antenna, a third electrical signal from the first sensor, and a fourth electrical signal from each of the plurality of second sensors, and convert each of the received second, third, and fourth signals that are readable by the controller,
wherein the plurality of tasks include:
a first determining task that receives the converted second electrical signal from the hardware interface and determines characteristics of the magnetic or electromagnetic field coupling between the antenna and the SM;
a repeating task that repeats the first determining task to obtain a plurality of characteristics of the magnetic or electromagnetic field coupling between the antenna and the SM at a predetermined interval over the evaluation period;
a second determining task that determines a shift in characteristics of the magnetic or electromagnetic field coupling between the antenna and the SM after each occurrence of the first determining task determining the characteristics of the magnetic or electromagnetic field coupling between the antenna and the SM at the predetermined interval, or collectively at the end of the evaluation period; and
a third determining task that determines a temporal change in relative displacement of the SM and determines the stiffness of the SM over the evaluation period, based on:
a first slope of a first deflection curve obtained from the plurality of second sensors versus an applied load curve obtained from the load sensor; and
a second slope of a second deflection curve obtained from the antenna versus the applied load curve.

14. The monitoring system according to claim 13, wherein the hardware interface is a network analyzer configured to:
output the first electrical signal to the antenna to induce the magnetic or electromagnetic field;

receive the second electrical signal from the antenna; and
also determine the characteristics of the magnetic or electromagnetic field coupling between the antenna and the SM based on the received second electrical signal.

15. A method of applying a load to measure stiffness of a structural member (SM) as the SM undergoes a displacement under a load, the method comprising:
providing a frame assembly including:
a lower support restable on a support;
a distal frame movable with respect to the lower support;
a plurality of first loading members disposed spaced on the distal frame along a longitudinal direction of the distal frame and configured to support the SM;
a plurality of SM support members disposed spaced on the lower support along a longitudinal direction of the lower support and configured to support the SM; and
at least one second loading member disposed between the plurality of SM support members and configured to be movable relative to the plurality of SM support members in a direction toward and away from the distal frame;
resting the SM on the plurality of SM support members;
lowering the distal frame toward the SM so that the plurality of first loading members apply a preload to the SM;
moving the at least one second loading member to apply a load to the SM and create multiple bending points with respect to the plurality of first loading members and the at least one second loading member;
measuring, using a first sensor, a load applied to the SM by the at least one second loading member;
measuring, using a plurality of second sensors, a first deflection of the SM undergoing loading;
measuring, using a third sensor, a second deflection of the SM undergoing loading without using any strain sensing device attached to the SM or contacting the SM,
wherein the stiffness of the SM is determinable from:
a first slope of a first deflection curve obtained from the plurality of second sensors versus an applied load curve obtained from the first sensor; and
a second slope of a second deflection curve obtained from the third sensor versus the applied load curve.

16. The method according to claim 15, wherein the distal frame is pivotable relative to the lower support to enable each of the plurality of first loading members to support the SM from one side while the plurality of SM support members support the SM from an opposite side to secure the SM between the plurality of first loading members and the plurality of SM support members.

17. The method according to claim 16, further comprising positioning the SM, using a movable stop member mounted to the lower support and configured to be adjustable along the longitudinal direction of the lower support to consistently position the SM on the loading device at different times.

18. The method according to claim 17, further comprising moving the lower support, which is movably disposed relative to the support toward the distal frame, so that the plurality of SM support members apply an additional preload to the SM.

19. The method according to claim 15, wherein the third sensor comprises an antenna disposed spaced from the SM, secured to the distal frame, and configured to:
induce, using a first electrical signal, a magnetic or electromagnetic field in the vicinity of the SM to create a coupling of the magnetic or electromagnetic field between the antenna and the SM, where characteristics of the magnetic or electromagnetic field coupling between the antenna and the SM are associated with a distance between the SM and the antenna; and
output a second electrical signal representing the magnetic or electromagnetic field coupling between the antenna and the SM, without using any strain sensing device directly attached to the SM.

* * * * *

UNITED STATES PATENT AND TRADEMARK OFFICE
CERTIFICATE OF CORRECTION

| | |
|---|---|
| PATENT NO. | : 11,717,213 B2 |
| APPLICATION NO. | : 17/039111 |
| DATED | : August 8, 2023 |
| INVENTOR(S) | : Christian M. Puttlitz and Kevin M. Labus |

It is certified that error appears in the above-identified patent and that said Letters Patent is hereby corrected as shown below:

In the Specification

In Column 1, Line 5, before the "BACKGROUND" section, please insert the following new paragraph:
--STATEMENT OF GOVERNMENT SUPPORT
This invention was made with government support under grant R21 AR077323 awarded by the National Institutes of Health. The government has certain rights in the invention.--

Signed and Sealed this
Third Day of September, 2024

Katherine Kelly Vidal
Director of the United States Patent and Trademark Office